United States Patent
Rininsland et al.

(10) Patent No.: US 11,851,698 B2
(45) Date of Patent: *Dec. 26, 2023

(54) METHOD FOR PATHOGEN IDENTIFICATION

(71) Applicant: Mesa Photonics, LLC, Santa Fe, NM (US)

(72) Inventors: Frauke Henrike Rininsland, Santa Fe, NM (US); Daniel James Kane, Santa Fe, NM (US)

(73) Assignee: MESA PHOTONICS, LLC, Santa Fe, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/105,864

(22) Filed: Feb. 5, 2023

(65) Prior Publication Data

US 2023/0272450 A1 Aug. 31, 2023

Related U.S. Application Data

(63) Continuation of application No. 17/380,862, filed on Jul. 20, 2021, now Pat. No. 11,603,552.

(51) Int. Cl.
*C12Q 1/37* (2006.01)
*G01N 33/569* (2006.01)

(52) U.S. Cl.
CPC ......... *C12Q 1/37* (2013.01); *G01N 33/56983* (2013.01); *G01N 2333/165* (2013.01); *G01N 2333/9513* (2013.01)

(58) Field of Classification Search
None
See application file for complete search history.

(56) References Cited

U.S. PATENT DOCUMENTS

| | | |
|---|---|---|
| 4,952,493 A | 8/1990 | Kettner et al. |
| 7,635,557 B2 | 12/2009 | Arad |
| 7,879,574 B2 | 2/2011 | Packard et al. |
| 10,962,529 B1 | 3/2021 | Alhadrami et al. |
| 11,603,552 B2 * | 3/2023 | Rininsland ........... G01N 33/533 |
| 2005/0267071 A1 | 12/2005 | Freire et al. |

(Continued)

FOREIGN PATENT DOCUMENTS

| | | |
|---|---|---|
| CN | 1690691 A | 11/2005 |
| CN | 101500591 A | 8/2009 |

(Continued)

OTHER PUBLICATIONS

AAT Bioquest-Stratech, "CovidyteTM Peptide Substrate Series Developed for Researchers in the Fight Against Covid-19," https://www.stratech.co.uk/aat-bioquest/research-solutions-for-coronavirus-14/#1601910984646-5425c0e2-5762, Jul. 6, 2021.

(Continued)

*Primary Examiner* — Shanon A. Foley

(57) ABSTRACT

The present invention relates to a method for detecting a pathogen in cellular lysate by measuring pathogen-specific enzyme activity. The method comprises contacting the cellular lysate with a substrate the pathogen of interest recognizes and modifies, and obtaining a measurable, recordable, signal. The method may comprise detection of SARS-CoV viruses using the activity of SARS PLpro enzyme in tongue scrape lysate as a readout.

23 Claims, 17 Drawing Sheets

Specification includes a Sequence Listing.

(56) References Cited

U.S. PATENT DOCUMENTS

| | | | |
|---|---|---|---|
| 2008/0241820 A1* | 10/2008 | Krutzik | G01N 33/537 435/7.1 |
| 2009/0305296 A1 | 12/2009 | Bengtsson et al. | |
| 2019/0056395 A1 | 2/2019 | Nobile et al. | |
| 2020/0286597 A1 | 9/2020 | Stahl | |

FOREIGN PATENT DOCUMENTS

| | | |
|---|---|---|
| CN | 102021145 B | 5/2013 |
| CN | 111334555 A | 6/2020 |
| CN | 111875709 A | 11/2020 |
| CN | 112461802 A | 3/2021 |
| EP | 0428000 A1 | 5/1991 |
| KR | 100304133 B1 | 11/2001 |
| KR | 20120081768 A | 7/2012 |
| KR | 101418898 B1 | 7/2014 |

OTHER PUBLICATIONS

Baez-Santos, Yahira M, et al., "Catalytic Function and Substrate Specificity of the Papain-like Protease Domain of Nsp3 From the Middle East Respiratory Syndrome Coronavirus," J. Virol. vol. 88 No. 21, Aug. 20, 2014, 12511-12527.

BPS Bioscience, "Papain-like Protease (sars-cov-2) Assay Kit: Protease Activity," https://bpsbioscience.com/papain-like-protease-sars-cov-2-assay-kit-protease-activity-79995, Jul. 5, 2021.

Chaudhuri, Rima, et al., "Comparison of SARS and NL63 Papain-Like Protease Binding Sites and Binding Site Dynamics: Inhibitor Design Implications," J. MoL. Biol. 414, Sep. 29, 2011, 272-288.

Cho, Jinhong, et al., "Assay Systems for Profiling Deubiquitinating Activity," Int. J. Mol. Sci. 2020, 21, 5638, Aug. 6, 2020.

Drag, Marcin, et al., "Positional-scanning Fluorogenic Substrate Libraries Reveal Unexpected Specificity Determinants of Deubiquitinating Enzymes (dubs)," Biochem. J. 415(3): 367-375, Nov. 1, 2008.

Geurink, Paul P, et al., "Profiling Dubs and Ubl-specific Proteases With Activity-based Probes," Methods Enz. vol. 618, 2019, 357-387.

Gurrieri, Vin, "Making Antibody Tests Optional Won't Erase Legal Risks," Law360 https://www.law360.com/publicpolicy/articles/1286353/making-antibody-tests-optional-won-t-erase-legal-risks?nl_pk=0ae55b4a-02af-40a8-80c4-4446b8d2a0d4&utm_source=newsletter&utm_medium=email&utm_campaign=publicpolicy, Jun. 6, 2020.

Hartley, M.Gillian, et al., "The Tongue Microbiota of Low Odour and Malodorous Individuals," Microbial Ecology in Health and Disease 9, 1996, 215-223.

Iwai, Shoko, et al., "Oral and Airway Microbiota in HIV-infected Pneumonia Patients," J. Clin. Microbiol. 50(9), Jul. 3, 2012, 2995-3002.

Jack, Benjamin R, et al., "Functional Sites Induce Long-Range Evolutionary Constraints in Enzymes," PLOS Biol. 14, el002452, May 3, 2016.

Jones, Garth, et al., "Resonance Energy Transfer: From Fundamental Theory to Recent Applications," Front. Phys. vol. 7, Art 100, Jul. 12, 2019.

Kucirka, Lauren M, et al., "Variation in False-Negative Rate of Reverse Transcriptase Polymerase Chain Reaction-Based SARS-CoV-2 Tests by Time Since Exposure," Annals of Internal Medicine M20-1495 (2020) doi:10.7326/M20-1495, May 13, 2020.

Li, Mengxia, et al., "Structure of the multiple functional domains from coronavirus nonstructural protein 3," Emerging Microbes & Infections 2021, vol. 10, 2021, 66-80.

Ma, Chunlong, et al., "Discovery of SARS-CoV-2 Papain-like Protease Inhibitors through a Combination of High-Throughput Screening and a FlipGFP-Based Reporter Assay," ACS Publications; https://doi.org/10.1021/acscentsci.1c00519, Mar. 16, 2021.

Oosterveer, M.A.P., et al., "Characterization of Epstein-barr Viral Strains in Parotid Gland Saliva and Peripheral Blood of Patients With Primary Sjogren's Syndrome and Healthy Ebv Carriers," J. Med. Virol. 41, 1993, 261-269.

Pachetti, Maria, et al., "Emerging SARS-CoV-2 mutation hot spots include a novel RNA-dependent-RNA polymerase variant," J. Transl. Med. 18:179, Apr. 22, 2020.

Petrosillo, N., et al., "COVID-19, SARS and MERS: are they closely related?," Clin. Microbiol. Infect. 26, Mar. 28, 2020, 729-734.

Ratia, Kiira, et al., "Structural Basis for the Ubiquitin-Linkage Specificity and deISGylating Activity of SARS-CoV Papain-Like Protease," PLOS Pathog. vol. 10, Issue 5 e1004113, May 22, 2014.

Reuters, "FDA grants emergency use authorization to Quidel for first antigen test for COVID-19," Reuters, https://www.reuters.com/article/us-healthcare-coronavirus-quidel-antigen/fda-grants-emergency-use-authorization-to-quidel-for-first-antigen-test-for-covid-19-idUSKBN22LON 6, May 9, 2020.

Rut, Wioletta, et al., "Activity Profiling and Crystal Structures of Inhibitor bound Sars-cov-2 Papain-like Protease: a Framework for Anti-covid-19 Drug Design," Science Advances 6(42): eabd4596, Oct. 16, 2020.

Rut, Wioletta, et al., "Activity profiling and structures of inhibitor-bound SARS-CoV-2-PLpro protease provides a framework for anti-COVID-19 drug design," https://doi.org/10.1101/2020.04.29.068890, Version 2, May 15, 2020.

Rut, Wioletta, et al., "Activity profiling of SARS-CoV-2-PLpro protease provides structural framework for anti-COVID-19 drug design," https://www.biorxiv.org/content/10.1101/2020.04.29.068890v1?versioned=true, Apr. 29, 2020.

Rut, Wioletta, et al., "Engineered Unnatural Ubiquitin for Optimal Detection of Deubiquitinating Enzymes," Chemical Science 11, May 27, 2020, 6058-6069.

Swatek, Kirby N, et al., "Irreversible Inactivation of Isg15 by a Viral Leader Protease Enables Alternative Infection Detection Strategies," Proc. Natl. Acad. Sci. vol. 115 No. 10, Mar. 6, 2018, 2371-2376.

Tian, Xufan, et al., "Characterization of Selective Ubiquitin and Ubiquitin-like Protease Inhibitors Using a Fluorescence-based Multiplex Assay Format," Assay and Drug Development Technologies 9(2), Apr. 2011, 165-173.

U.S. Dept of Health & Human Serv, "2019-Novel Coronavirus (2019-nCOV) Real-time rRT-PCR Panel Primers and Probes for COVID-19," CDC https://www.cdc.gov/coronavirus/2019-ncov/lab/rt-pcr-panel-primer-probes.html, May 29, 2020.

Wang, Chen, et al., "A novel coronavirus outbreak of global health concern," The Lancet vol. 395, Jan. 24, 2020, 470-473.

Weglarz-Tomczak, Ewelina, et al., "Ebselen as a Highly Active Inhibitor of PI Pro Cov2," bioRxiv preprint DOI: 10.1101/2020.05.17.100768, May 17, 2020.

Wei, Shan, et al., "Field-deployable, rapid diagnostic testing of saliva samples for SARS-CoV-2," medRxiv https://www.medrxiv.org/content/10.1101/2020.06.13.20129841 vl, Jun. 16, 2020.

West, Colin P, et al., "COVID-19 Testing: The Threat of False-Negative Results," Mayo Clinic Proc. 95, Jun. 2020, 1127-1129.

Xu, Hao, et al., "High expression of ACE2 receptor of 2019-nCo V on the epithelial cells of oral mucosa," Int. J. Oral Sci. 12, 8, Feb. 24, 2020.

Xu, Jiabao, et al., "Systematic Comparison of Two Animal-to-Human Transmitted Human Coronaviruses: SARS-CoV-2 and SARS-CoV," Viruses 2020, 12, 244, Feb. 22, 2020.

Ye, Qing, et al., "The pathogenesis and treatment of the Cytokine Storm in COVID-19," J. Infect. 80, Apr. 10, 2020, 607-613.

Zaki, Ali Moh, et al., "Isolation of a Novel Coronavirus from a Man with Pneumonia in Saudi Arabia," N. Engl. J. Med. 367; 19, Oct. 17, 2012, 1814-1820.

Zhao, Yao, et al., "High-throughput Screening Identifies Established Drugs as Sars-cov-2 Plpro Inhibitors," Protein & Cell 2021, Apr. 17, 2021.

Zhong, N. S., et al., "Epidemiology and cause of severe acute respiratory syndrome (SARS) in Guangdong, People's Republic of China, in Feb. 2003," The Lancet vol. 362, Oct. 25, 2003, 1353-1358.

"COVID-19 Map," Johns Hopkins Coronavirus Resource Center, https://coronavirus.jhu.edu/map.html, Jun. 25, 2020.

(56) References Cited

OTHER PUBLICATIONS

Borodovsky, Anna, et al., "Small-Molecule Inhibitors and Probes for Ubiquitin- and Ubiquitin-Like-Specific Proteases," ChemBioChem 2005, 6, 287-291, Jan. 13, 2005.

Cui, Jie, et al., "Origin and evolution of pathogenic coronaviruses," Nat Rev Microbiol. 2019; 17(3):181-192, Dec. 10, 2018.

Huang, Chaolin, et al., "Clinical features of patients infected with 2019 novel coronavirus in Wuhan, China," The Lancet. 2020;395(10223):497-506, Feb. 15, 2020.

La Scola, Bernard, et al., "Viral RNA load as determined by cell culture as a management tool for discharge of SARS-CoV-2 patients from infectious disease war," Eur J Clin Microbiol Infect Dis. 2020; 39(6):1059-1061, Apr. 27, 2020.

Li, Dandan, et al., "Primer design for quantitative real-time PCR for the emerging Coronavirus SARS-CoV-2," Theranostics. 2020; 10(16):7150-7162, Jun. 1, 2020.

Market Study Report, LLC, "Global COVID-19 diagnostic testing market to amass USD 44481.8 million in 2020," https://www.globenewswire.com/news-release/2020/06/01/2041269/0/en/Global-COVID-19-diagnostic-testing-market-to-amass-USD-44481-8-million-in-2020.html, Jun. 1, 2020.

Ranoa, Diana Rose E, et al., "Saliva-Based Molecular Testing for SARS-CoV-2 that Bypasses RNA Extraction," Microbiology; 2020, Jun. 18, 2020.

Soboleva, Tatiana A, et al., "Deubiquitinating Enzymes: Their Functions and Substrate Specificity," Curr Protein Pept Sci. 2004; 5(3):191-200, Jul. 2004.

Soleimany, Ava P, et al., "Activity-Based Diagnostics: An Emerging Paradigm for Disease Detection and Monitoring," Trends Mol Med. 2020; 26(5):450-468, May 2020.

Walsh, Kieran A, et al., "SARS-CoV-2 detection, viral load and infectivity over the course of an infection," J Infect. 2020; 81(3):357-371, Jun. 29, 2020.

Zhang, Ji-Hu, et al., "A Simple Statistical Parameter for Use in Evaluation and Validation of High Throughput Screening Assays," J Biomol Screen. 1999; 4(2):67-73, 1999.

Zhou, Peng, et al., "A pneumonia outbreak associated with a new coronavirus of probable bat origin," Nature. 2020; 579(7798):270-273, Feb. 3, 2020.

\* cited by examiner

METHOD FOR PATHOGEN IDENTIFICATION

CROSS-REFERENCE TO RELATED APPLICATIONS

The present application claims priority to U.S. patent application Ser. No. 17/380,862 entitled "Method for Pathogen Identification," filed Jul. 20, 2021, which application is incorporated by reference in its entirety. The present application also incorporates by reference U.S. provisional patent application Ser. No. 63/053,964, entitled "Method for Identifying Pathogens for Measurement Thereof," filed on Jul. 20, 2020.

STATEMENT REGARDING FEDERALLY SPONSORED RESEARCH

This invention was made with government support under contract number SP4701-21-P-0021. The U.S. government has certain rights in the invention.

SEQUENCE LISTING

The present application contains a sequence listing file, Pathogen_ID.xml created on May 13, 2023, 9 KB in size, which has been submitted electronically in XML format as part of this application, and which is hereby incorporated by reference in its entirety.

BACKGROUND OF THE INVENTION

Field of the Invention (Technical Field)

Embodiments of the present invention relate to a method for determining enzymatic activity in a sample and a sample preparation protocol. The invention is relevant to the field of diagnostics; biological and enzymological research; and pharmacology and medicine.

DESCRIPTION OF RELATED ART

Coronaviruses (CoVs) belong to the subfamily of Coronavirinae within the family Coronaviridae and the order Nidovirales. Coronaviruses are enveloped viruses with a single stranded, non-segmented and positive RNA of 27 to 31 kb. The family of Coronaviridae consists of four genera: Alphacoronavirus (Alpha-CoV), Betacoronavirus (Beta-CoV), Gammacoronavirus (Gamma-CoV) and Deltacoronavirus (Delta-CoV). Most of the mammalian CoVs belong to Alpha- and Beta-CoV, whereas the avian and the cetacean CoVs are in the Gamma-CoV.

Coronaviruses enter human host cell through specific attachment to receptors on host cells. SARS-CoV-1, SARS-CoV-2 and NL63 coronaviruses enter cells by binding to the specific host cell receptor ACE2, which is highly expressed on epithelial cells of the gastrointestinal tract, lung, and cells of the oral cavity, such as the tongue. In contrast, the Middle East respiratory coronavirus (MERS) enters cells via the DPP4 receptor, 229E via CD13, HKU1 and 0043 via sialic acid. SARS viruses may enter cells through other receptors, such as CD147 or others not yet identified.

Three global epidemics of human coronaviruses have so far emerged in this century. In 2002, infections with severe acute respiratory syndrome coronavirus (SARS-CoV-1) were reported in China. Ten years later the Middle East respiratory syndrome coronavirus (MERS-CoV) appeared in Saudi Arabia and spread worldwide. In December 2019, a novel coronavirus—severe acute respiratory syndrome coronavirus 2 (SARS-CoV-2)—was identified in Wuhan, China. Current studies indicate that this coronavirus is similar to SARS-CoV-1. The main symptoms of these coronavirus infections are similar to influenza-like complaints and include fever, headache, malaise, shivering and diarrhea. SARS-CoV-2 also infects the lower respiratory tract (bronchial tubes and the lungs) where it can trigger an inflammatory response as the body produces antibodies and T cells to fight the virus. Around 15% of people experience an overreaction of their body's immune system, called a cytokine storm. This can severely damage the lungs, kidney and heart and cause clot formation, causing some people to become severely ill or die.

With a fatality rate of ~2.3%, SARS-CoV-2 is much less fatal than SARS-CoV-1 (9.5%) or MERS (34.4%). However, because initial symptoms of COVID are benign, the virus spreads more easily among asymptomatic carriers before they experience symptoms.

Coronaviruses (CoVs) are also documented in a wide range of plant and animal species, including terrestrial and aquatic, domestic and wild. The animal viruses are known to cause mainly gastrointestinal and respiratory diseases with different severity levels. In certain cases, CoV infections are responsible for huge economic losses. Coronaviruses affecting livestock and other animals include bovine coronavirus (cattle), bulbaline coronavirus (buffalo), Middle East respiratory syndrome coronavirus (MERS; dromedaries), equine coronavirus, rabbit coronavirus, porcine hemagglutinating encephalomyelitis virus (PHEV), transmissible gastroenteritis virus (porcine TGEV), porcine respiratory coronavirus (PRCV), swine acute diarrhea syndrome coronavirus (SADS-CoV), porcine epidemic diarrhea virus (PEDV), porcine delta coronavirus (PDCoV), infectious bronchitis virus (IBV; chicken), dolphine bottlenose whale (BdCoV), beluga whale (BWCoV), and harbor seal coronavirus. Other animals that harbor coronaviruses are cats, dogs, mink, tigers, gorillas, and others.

Enzymes are proteins that catalyze chemical or biological reactions by lowering the activation energy of a chemical and/or biological reaction. Thousands of different enzymes exist. The molecules upon which enzymes may act are called substrates, and the enzyme converts the substrates into different molecules known as products. Enzymes specifically recognize their substrates and form an enzyme-substrate complex. Binding brings the substrate into a favorable conformation for a reaction to occur. The enzymes can thus accelerate up to millions of times the chemical reactions. Like any catalyst, enzymes are neither consumed in chemical reactions, nor do they alter the equilibrium of a reaction.

Enzymes differ from most other catalysts by their specificity for the substrates they modify. Enzyme activity can be affected by other molecules: inhibitors are molecules that decrease enzyme activity and activators are molecules that increase activity. Many therapeutic drugs and poisons are enzyme inhibitors.

Proteolytic enzymes that cleave a protein or peptide substrate are called proteases. Proteases are essential for the biological function of viruses, eukaryotes, and prokaryotes. Proteolytic enzymes hydrolyze amides and esters to produce peptides or single amino acids. Protease activity can be measured using naturally occurring substrates or, for example, using a synthetic peptide substrate with an amino acid sequence the protease of interest recognizes. The peptide can be labeled with a reporter molecule, such as a fluorescent probe or a chromophore. In some cases, the protease activity can be measured using a labeled single amino acid. The protease activity is measured by the ability of the protease to cleave the bond between an amino acid and the reporter label.

Papain-like proteases are multifunctional enzymes that are essential to viral replication. After a coronavirus enters a cell, it releases its RNA and hijacks the host replication machinery to translate its RNA into two polyproteins, pp1a and pp1ab. The polyproteins are cleaved into 16 non-structural proteins (nsps) by the SARS main protease (3CL-Pro) and either one or two viral papain-like proteases. Human coronaviruses SARS-CoV-1, SARS-CoV-2, and MERS contain only one papain-like protease (PLpro), whereas HCoV-HKUI, HCoV-0C43, HCoV-NL63 and HCoV-229E contain two protease domains, PLP1 and PLP2, that process the polyprotein. The PLpro substrate binding site recognizes three cleavage sequences in the polyprotein pp1 that share the highly conserved consensus sequence R-L-X-G-G (SEQ ID NO. 4) where X is any amino acid.

PLpro and PLPs have not only proteolytic but also deubiquitinating (DUB) and delSGylating activities that counteract the post-translational modification of signaling molecules that activate the innate immune response. The amino acids that are responsible for these modifications form the catalytic core of PLpro/PLP and are highly conserved. However, the overall amino acid identity in papain-like proteases is low (18-32%). The substrate binding sites in different PLpros/PLPs have different preferences for various ubiquitins and Interferon Stimulated Gene 15 (ISG15).

Ubiquitin (Ub) is a 76 amino acid protein that is covalently attached to a substrate via the terminal glycine residue in L-X-G-G of Ub via an isopeptide bond to a lysine or N-terminal amino group on the substrate. Substrate-conjugated ubiquitins can be further modified by additional attachment of ubiquitins to Ub lysine residues or to the Ub N terminus to form, for example, K6, K11, K27, K29, K33, K48 and K63 linked branched di-ubiquitins, where K is lysine, and the number denotes the position of the lysine within ubiquitin. Multiple conjugations are also possible, e.g., K48/K63, K6/K11 or combinations of K6, 11, 27, 29, 33, 48, 63. Enzymes, such as PLpro, remove ubiquitin by cleaving the terminal L-X-G-G sequence that links the substrate and ubiquitin.

ISG15 is a linear bi-ubiquitin with the distinctive L-X-G-G motif at its C terminus for attachment to target proteins. Deubiquitylating enzymes, such as PLpro, remove ISG15 by cleaving the terminal L-X-G-G sequence that links the substrate and ISG15.

Table 1 shows the ubiquitin and ISG15 substrate preferences of some PLpros/PLPs from various viruses known to infect humans. The differences in preferences can be used to identify the presence of a specific virus.

TABLE 1

Various human viruses and their ability to cleave ISG15 and/or various linear or branched ubiquitins.

| | K48 | K48/K63 | K63 | K6/11 | ISG15 |
|---|---|---|---|---|---|
| Adenovirus | ✓ | | | | ✓ |
| Herpes Simplex virus 1 | ✓ | | ✓ | | |
| Human Cytomegalovirus | | ✓ | | | |
| Epstein Barr Vims | | ✓ | | | |
| Kaposi Sarcoma | | ✓ | | | |
| SARS-1 | ✓ | | ✓ | | ✓ |
| SARS-2 | ✓ | | | | ✓ |
| MERS | ✓ | | ✓ | | ✓ |
| NL63 | | ✓ | | | ✓ |
| Crimean Congo Hemorrhagic Fever Virus (CCHFV) | | ✓ | ✓ | ✓ | ✓ |
| Dugbe Virus (DUGV) | ✓ | ✓ | ✓ | ✓ | ✓ |
| Endogenous Retrovirus Group V (ERVV) | | | | | ✓ |

Other virus with enzymes capable of removing ISG15 and/or ubiquitin that infect animal hosts or plants include the infectious bronchitis virus (IBV; chicken), equine arteritis virus (EAV), porcine reproductive and respiratory syndrome virus (PRRSV), lactate-dehydrogenase elevating virus (LDV; mouse), simian hemorrhagic fever virus (SHFV), Nairobi sheep disease virus (NSDV), foot and mouth disease virus (FMDV), and turnip yellow mosaic virus (TYMV).

SARS-CoV-1, SARS-CoV-2, and MERS cause severe respiratory disease while the four common human coronaviruses (HCoV) 229E, OC43, NL63 and HKU1 generally cause mild to moderate upper-respiratory illness in 15%-30% of cases of common colds. For accurate diagnosis, it is essential to identify the type of causative coronavirus. The different preferences for ubiquitin types and ISG15 substrates among the members of human coronaviruses opens up the possibility of distinguishing between the strains by screening different substrates and obtaining "fingerprints" that are distinct for each of the seven human coronaviruses, shown in Table 2.

TABLE 2

Six of seven coronavirus strains known to infect humans and their subgroups are listed. The cleavage of 4 different papain-like protease substrates is indicated by "+" where each additional "+" roughly corresponds to a 10-fold increase in activity using recombinant enzyme.

| Coronavirus | Subgroup | Ty-Dap-G-G | L-R-G-G (SEQ ID NO. 1) | Ubiquitin | ISG15 | Enzyme |
|---|---|---|---|---|---|---|
| MERS | β | — | + | ++ | +++ | recombinant |
| SARS-1 | β | ++ | ++ | ++ | +++ | recombinant |
| SARS-2 | β | + | + | ++ | +++ | recombinant |
| OC43 | β | 34%[3] | 22%[2] | — | 38%[1] | viral, in vivo |
| 229E | α | — | — | — | 42.4%[1] | viral, in vivo |
| NL63 | α | — | — | 24%[1] | — | viral, in vivo |
| NL63 | α | — | — | +++ | ++ | recombinant |

[1, 2, 3] = measurement taken after 15, 60, or 800 minutes of incubation, respectively.

The catalytic rates differ among coronaviruses and correspond to the number of substrates that are turned over to form product. They are given as Kcat (min$^{-1}$) in Table 3 shown before for various coronaviruses.

TABLE 3

Catalytic rates (Kcat) of various coronaviruses. Rates with which tetrapeptide L-R-G-G (SEQ ID NO. 1), ubiquitin and ISG15 are converted are given in in min$^{-1}$.

| Coronavirus | Tetrapeptide | Ubiquitin | ISG15 |
|---|---|---|---|
| SARS-1 | 0.0051 | 10 | 40 |
| SARS-2 | 0.3 | 75.9 | 436 |
| MERS | 0.003 | 18.8 | 32.6 |

Coronaviruses show a moderate mutation rate of 10$^{-4}$ nucleotide substitutions/site/year. Twenty-seven of the proteins comprising the SARS-CoV-2 virus are mutating at different rates, with the principal targets of COVID-19 vaccines and therapeutics, the Spike and Nucleocapsid proteins, having the highest mutational variability. In contrast, the mutation rates in SARS enzymes are low, which is expected because enzymes must fold into precise three-dimensional structures to function. Within that structure specific amino acids are brought together to form substrate binding sites, catalytic sites, and binding sites for cofactors, collectively known as active sites. These clusters of functional residues are highly conserved to ensure that only intended substrates are bound and chemically modified in the intended way. Active sites of enzymes are the most highly conserved sites in proteins. Although enzymes are just as subject to random mutations as structural proteins, mutations that change the three-dimensional structure of an enzyme or the amino acid sequence of its active sites lead to loss of function and nonviable virus. The mutational frequency in the nonstructural proteins cleaved by PLpro—and in PLpro itself—are significantly lower than those observed in the spike protein (S) and nucleocapsid (N) protein.

Detection methods conventionally used for the detection of pathogens are, for example, Polymerase Chain Reaction (PCR) and antigen tests. RT-PCR is the current "gold standard" for detection of pathogens, such as SARS-CoV-2. PCR amplifies specific DNA targets so they can be visualized at the end of the reaction or while the reaction progresses in real-time. If the genetic material of the virus is RNA, as in the case of coronaviruses, the RNA first has to be converted into complementary cDNA using reverse transcriptase (RT). The cDNA is then used as a template for exponential PCR amplification. PCR employs two primers with sequences that are complementary to the target cDNA and a DNA polymerase that assembles new strands of DNA from free nucleotides. In addition to the two amplification primers, real time PCR uses a probe that binds specifically to a region of the DNA that is being amplified. The probe is labeled with a quencher and a fluorophore that fluoresces when the polymerase removes the probe from the DNA strand and cleaves it. The amount of fluorescence correlates with the amount of DNA being produced and can be observed in real time.

The relationship between SARS-CoV-2 detection, viral load, and infectivity is not fully understood, as viral material that is detectable by RT-PCR or antigen tests may not represent transmissible live virus, but prolonged shedding of non-viable viral fragments. For example, viable virus able to infect cell cultures was not found in samples collected after day eight of symptom onset, in spite of ongoing high viral loads of approx. 10$^5$ RNA copies/mL that gave positive results with RT-PCR. In other words, the detection of viral RNA does not necessarily mean that a person is infectious and able to transmit the virus to another person. Information about the actual duration of infectivity is important so RT-PCR positive but non-infectious people can return to their normal activities, correct assignments in hospital wards can be made, and treatment options pursued. For example, lung transplants can be made only after COVID-19 patients test negative with RT-PCR.

Current methods to determine the presence of infectious virus are indirect, time consuming, and complex. In laboratory experiments virus supernatants are transferred onto host cells, such as Vero E6 cells, and incubated for around 70 h. Cytopathogenic effects of viral infection are scored visually or by determining the remaining metabolic activity of the infected cells. This approach is not practical in clinical settings.

The FDA has approved over 200 SARS RT-PCR tests. RT-PCR can, in theory, detect one molecule of viral RNA, and has become the gold standard for COVID-19 testing. Other nucleic-acid based test systems include RT-LAMP (RT loop-mediated isothermal amplification), CRISPR (Clustered Regularly Interspaced Short Palindromic Repeats), or SPOT (Scalable and Portable Testing).

These tests share an Achilles heel: their target biomolecule is viral RNA (ribonucleic acid) that must first be transcribed into deoxyribonucleic acid (DNA) for molecular tests to perform. Unfortunately, RNA is extremely unstable and prone to rapid degradation during sampling, shipment, and purification. As a result, despite a theoretical analytical sensitivity of less than 5 viral copies of purified RNA reported for some of the RT-PCR tests, the limits of detection (LoD) in clinical samples vary greatly (500-80,000 copies/ml).

The COVID-19 pandemic has left approximately 176 million people infected with SARS-CoV-2 and over 3.8 million dead. Variants that can evade detection are quickly emerging from the enormous reservoir of infected people. New mutations in the SARS-CoV-2 genome increase RT-PCR false-negative test results when primer and probes bind weakly, or no longer at all, to the mutated sequences. Although RT-PCR tests amplify cDNA from several regions of the SARS genome that generally do not all fail at the same time, one variant in France was completely undetectable by RT-PCR. But even if only one PCR product is absent, an "inconclusive" result is triggered, and the test must be repeated by a different test or sequencing.

The rate of reported false negative SARS-CoV-2 results are at between 20% to 67% in clinical samples, depending on the viral load at the time of testing. Aside from the instability of RNA, the inadequate sample collection is another reason for high false negative rates. Nasopharyngeal (NP) swabs may miss virus, i.e., the swab may not be inserted deeply and/or broadly enough in the nasopharyngeal cavity to capture viruses. Collection of other specimen types, such as sputum, nasal swab, and throat swab is rapid, simple, and safe but the precision remains to be determined.

Other disadvantages of RT-PCR are:

1. RT-PCR tests require sophisticated equipment that cost between USD 15,000-USD 90,000 and trained personnel at centralized locations;
2. The test can detect inactive viral fragments remaining from a previous infection, complicating treatment decisions that rely on an infection-free status, e.g., for lung transplants;
3. Primer and probe binding are affected by changes in viral RNA sequences, and this variability can cause mismatches between primers and probes and the target sequence, leading to decrease in assay performance and false negative results;
4. Samples contain live virus and because of the infection risk, sampling and testing require personnel protective equipment;
5. It can take days for results to be reported; and
6. Because it contains numerous difficult-to-produce components, such as enzymes and viral transport media, RT-PCR is difficult to scale up.

Antigen tests are typically inexpensive and return results in minutes. Antigen tests can detect the presence of a viral protein in a biological sample, such as a NP swab. Generally, drops of the sample are spotted on a surface, such as a plastic well or a test strip, that is coated with one antibody that binds the SARS protein (the capture antibody) and another that detects it (the detection antibody). If both antibodies bind, a signal is generated, such as a color change, that can be read visually although some setups use small readers to improve the accuracy. The challenge with antigen tests is finding antibodies that both bind to the single viral protein, such as the SARS-CoV-2 spike protein, at separate sites, but do not cross react with other coronaviruses or bind nonspecifically.

Weak signals are a major drawback because antigen tests do not amplify the protein signal; therefore, they are inherently less sensitive than RT-PCR or enzyme assays. As a result, most antigen tests have a detection sensitivity of between 50% and 90%, relative to RT-PCR.

In addition to a high false-negative rate of detection, antigen tests share some of the disadvantages of RT-PCR tests, namely that they can detect inactive virus and the capture and/or detection antibody may no longer bind when viral antigens mutate.

Serological tests detect antibodies developed against the SARS-CoV-2 in the blood of infected people. These tests can help identify individuals who have mounted an immune response to the virus as part of either an active or prior infection. Antibodies against SARS-CoV-2 take 1-3 weeks to develop in the bodies of those infected; therefore, detecting an antibody response is not suitable for diagnosing active infections. In addition, the false-positive detection rate through antibody binding to similar proteins from other coronaviruses is possible and remains to be determined. Further, there is not enough information yet to determine whether antibody-positive individuals will be immune and protected from reinfection and therefore be safe to reenter society without spreading the disease. Moreover, recent legal rulings prohibit employers from requiring employees to take serological tests as a condition for returning to work following possible exposure because the tests cannot unambiguously identify healthy from ill people. What is needed is a method for detecting pathogens that on-site, rapid, reproducible with large volumes of samples, and is accurate.

Natural, therapeutic, or vaccine-derived antibodies can block ("neutralize") pathogens from infecting host cells by binding to proteins on the outside of pathogens that interact with host cell receptors. For example, antibodies against the SARS spike protein prevent the virus from binding to ACE2 receptors and from entering a cell. The antibody recognizes a specific amino acid sequence on the target protein (the antigen). Therefore, mutations in pathogen antigens can reduce or abolish antibody neutralizing activities when antibodies bind more weakly or no longer at all to the antigens.

Although COVID-19 vaccines have shown up to 95% efficacy in preventing infection with wildtype SARS-CoV-2, reports show that the South African variant has complete immune-escape in South African convalescent serum samples, and reductions in neutralizing activity in vaccinee serum samples for all four vaccines tested have been reported. Even more disturbing is the situation in Manaus, Brazil, where a second wave of infection due to a variant swept through a population that was already 76% seropositive owing to prior infection in the spring of 2020. Escape variants appear to be responsible for the surge in infections in some Indian cities where around 50% of the population had already been infected. Eight mutations in the spike protein have already been identified that are suspected of reducing the neutralizing activity of human antibodies raised against it by vaccines or natural immunity.

Therefore, it is expected that annual booster shots will be needed for COVID-19, like for the flu. Although large-scale Phase 3 clinical trials (including approx. 30,000 subjects) to test the safety and tolerability are not required for booster vaccines, the FDA still requires small clinical trials with around 300 subjects to ensure that the new vaccines have neutralizing activities. Vaccine developers test the efficacy of new vaccines against seasonal circulating strains by first measuring their neutralizing activity in the lab, and later in clinical trials. In the lab, virus—antibody mixtures are transferred onto host cells, incubated for around 70 h and cytopathogenic effects of viral infection determined. In clinical trials, the efficacy of the vaccine is determined by comparing the number of cases between the groups that received placebo or vaccine. Therefore, what is needed is a method for quickly detecting pathogens to more rapidly test vaccine efficacy.

Drugs that can inhibit the activity of pathogen enzymes and thereby prevent viral replication are promising therapeutics. The majority of high throughput or high content drug screens are performed using defined reaction conditions and recombinant enzymes in biochemical assays. The drawbacks of biochemical assays are that drugs with cytotoxic effects and/or poor cell permeability can be missed. Potential drawbacks of cell-based expression systems are that recombinant enzymes often behave differently than natural viral enzymes and exhibit different inhibition profiles. The spread of SARS-CoV-2 has stimulated the development of small molecule antiviral inhibitors to treat patients who do not accept or respond to vaccines. Drugs that can inhibit the activity of SARS enzymes and thereby prevent viral replication are promising therapeutics.

An affordable, simple, rapid, and on-site test such as the test according to the present invention is needed to identify and contain infections immediately, and thereby prevent further infections and mitigate an outbreak. What is also needed is a method to accelerate cell-based drug discovery by measuring the potencies of inhibitors against natural, unmodified enzymes. What is further needed is a method to screen scanning libraries using crude active lysates from cultured cells to quickly and efficiently identify peptides cleaved by an enzyme of interest with the least cleavage from endogenous host enzymes.

BRIEF SUMMARY OF EMBODIMENTS OF THE PRESENT INVENTION

The present invention relates to a method for identifying a pathogen, the method comprising: collecting a specimen, wherein the specimen comprises a cell; lysing the cell to form a cell lysate, wherein the cell lysate comprises an internal control; contacting the cell lysate with a substrate, wherein the substrate comprises a sequence of a natural pathogen protein that may be cleaved by a pathogen enzyme and wherein the substrate comprises a signaling moiety; cleaving the substrate; and simultaneously reading a signal from the substrate and internal control. In one embodiment, the specimen is a tongue scrape.

In another embodiment, the pathogen is a coronavirus. In another embodiment, the coronavirus is SARS-CoV-2. In another embodiment, the substrate is a peptide. In another embodiment, the peptide is 4 amino acids in length. In another embodiment, the peptide comprises the sequence L-R-G-G (SEQ ID NO. 1).

In another embodiment, the internal control comprises a peptide conjugated to a signaling moiety that produces a signal that can be differentiated from the signal of the substrate. In another embodiment, the internal control comprises ACE2.

In another embodiment, the pathogen enzyme is a protease. In another embodiment, the protease is PLpro.

In another embodiment, the method further comprises a calibrator. In another embodiment, the calibrator calibrates fluorescent and unconjugated signaling moieties. In another embodiment, the calibrator quantifies the amount of pathogen present in the cell lysate.

In another embodiment, the cleavage substrate is read in about 1 min to about 15 min. In another embodiment, the method is performed as a lateral flow assay. In another embodiment, the method further comprises cleaving the substrate to produce one peptidic and one non-peptidic fragment. In another embodiment, the method further comprises calculating the rate of substrate cleavage to identify the pathogen.

In another embodiment, the substrate comprises ubiquitins. In another embodiment, the cell lysate is crude. In another embodiment, the substrate comprises biological fragments and a 4-amino-acid peptide sequence.

In another embodiment, the method further comprises identifying a coronavirus variant from the substrate cleavage. In another embodiment, the signal indicates the presence of an active viral infection. In another embodiment, the signal indicates the presence of antibodies.

In another embodiment, the substrate comprises ubiquitin, ISG15, and a peptide comprising the amino acid sequence L-R-G-G (SEQ ID NO. 1). In another embodiment, the substrate is comprised within a competitive assay. In another embodiment, the ubiquitin and the ISG 15 are contacted with the peptide comprising the amino acid sequence L-R-G-G (SEQ ID NO. 1). In another embodiment, the ubiquitin and the ISG15 are conjugated to a substrate that comprises the amino acid sequence L-R-G-G (SEQ ID NO. 1).

In another embodiment, the substrate is derived from a mammal. In another embodiment, lysing the cells comprises contacting the cells with lysis buffer.

In another embodiment, the method of the present invention is easy to use, does not require specialized personnel or equipment, and has a minimal burden on logistics. The method may comprise reagents that may be chemically synthesized within days in bulk for millions of tests, allowing for widespread screening that helps prevent pathogen transmission and mitigates pathogen outbreaks.

In another embodiment, the method provides a simple positive or negative response and/or reading in less than 15 minutes. The method may be used to detect pathogens in humans, animals, and/or plants.

In another embodiment, the method comprises a signal generated when a peptide substrate is cleaved by a protease to produce one peptidic and one nonpeptidic fragment. The nonpeptidic fragment corresponds to the fluorophore that is now fluorescent.

In another embodiment, the method comprises an enzymatic assay. The enzymatic assay may detect cleaved substrate by fluorescent signals. The enzymatic assay may comprise a substrate labeled with a reagent and may be added directly to live cells or crude cell lysate. The substrate may enter cells or contact crude cell lysate and may be cleaved by endogenous enzymes. Cleavage may be observed in real time by monitoring the fluorescence increase. The substrate may be four amino acids in length and the enzyme may be PLpro. The enzymatic assay may further comprise an internal control. The internal control may comprise ACE2. In another embodiment, the substrate may be derived from different species to identify the pathogen.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
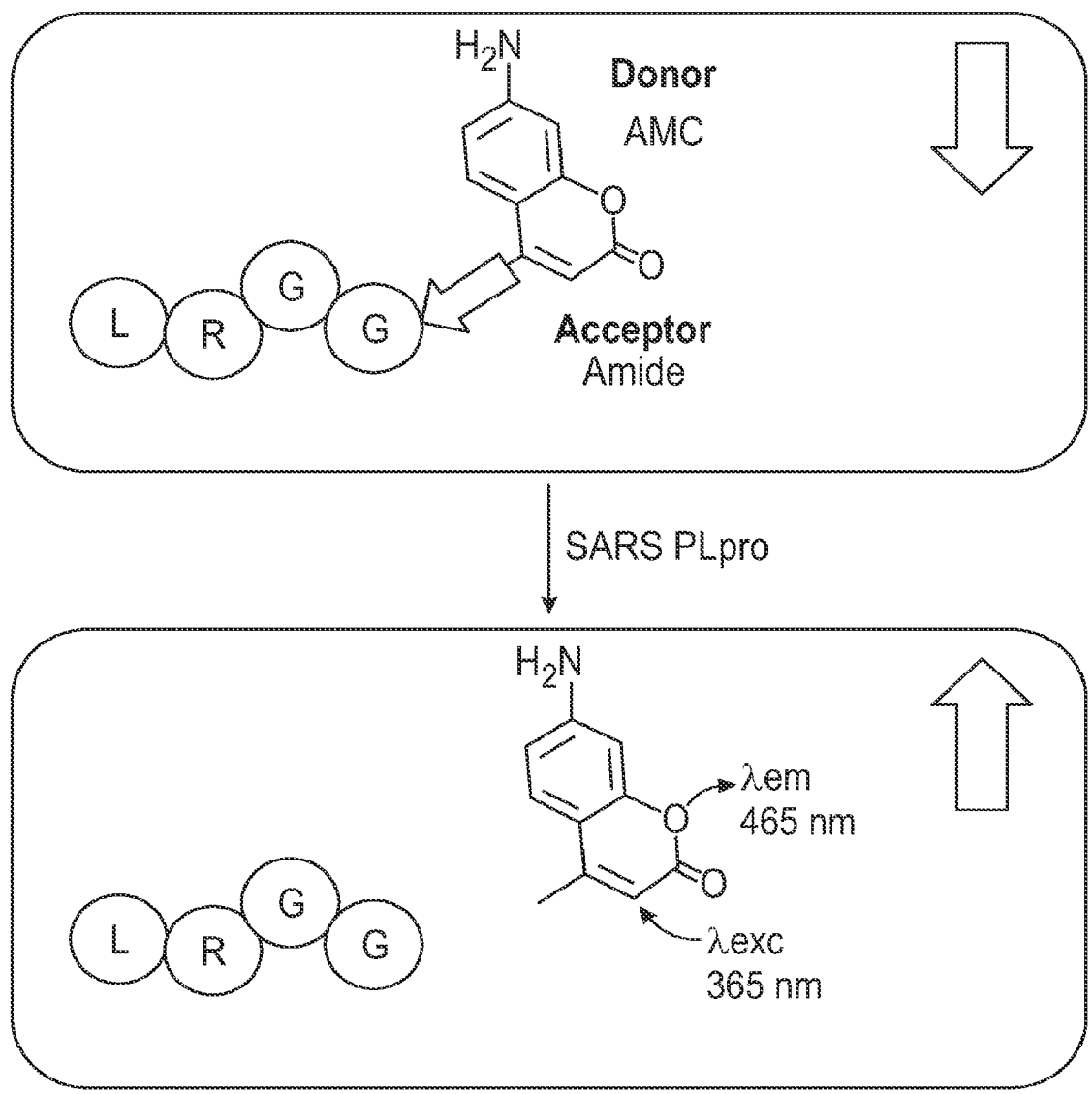
FIG. 1 is a schematic showing a quench mechanism based on electron transfer between donor and acceptor peptide SEQ ID NO. 1.

An embodiment of the present invention is directed to a method for an activity-based diagnostic (ABDx) for a rapid response platform capable of detecting pathogens by measuring the activities of enzymes that are unique for a given pathogen, for example, papain-like protease (PLpro) in SARS coronavirus-infected cells.

The term "enzyme" means any enzyme known to those skilled in the art. An enzyme may comprise a viral, prokaryotic, or eukaryotic enzyme. An enzyme may be present in a solution and/or biological solution, including, but not limited to, a tongue scrape cell mixture, saliva, sputum, blood, lymph, urine, feces, bodily fluid, or a combination thereof. The enzyme may be present in an extract. The extract may comprise, but is not limited to, any pathogen-infected cell, an extract of plants, bacterial or fungal cultures, or any biological extract.

The term "protease" means proteins that are known as proteinases or peptidases. Proteases are classified and/or defined on the basis of their catalytic mechanism into the following groups: serine proteases (S), cysteine proteases (C), aspartic proteases (A), metalloproteases (M), and Unknown, or as yet unclassified, proteases (U). Papain-like proteases (PLpro) belong to the class of cysteine proteases.

The term "substrate" means both naturally occurring substrates, and synthetic analogues of naturally occurring substrates comprising a substrate recognition sequence. Enzyme substrates mean any molecule comprising proteins, peptides, deoxyribonucleic acid (DNA), ribonucleic acid (RNA), lipids, carbohydrates, polyesters, polythioesters, polyisoprenoids, or a combination thereof. A substrate may be derived from a biological source. The biological source may comprise a mammal, a reptile, a bird, or a combination thereof. The mammal may comprise any mammalian species including, but not limited to, a bat, a sheep, a human, a pig, a cow, a goat, or a combination thereof.

The term "peptide" and "protein" may be used interchangeably and may comprise amino acid sequences of any length. The terms "peptide" and "protein" comprise molecules with naturally occurring, semi-synthetic, or artificial sequences, where amino acids may be comprised within artificial sequences that do not naturally occur in proteins. For example, the terms "peptide" and "protein" may refer to an amino acid sequence of a recombinant or non-recombinant peptide with an amino acid sequence of a native peptide; a biologically active fragment of a native peptide; a biologically active peptide analogue of a native peptide; a biologically active variant of a native peptide; a peptide having an artificial sequence comprising a biologically active consensus sequence; a peptide having a wholly artificial sequence; or a combination thereof. In general, the terms "protein", "peptide" and "amino acid" are to be interpreted broadly to encompass any derivative molecules that provide one or more bonds capable of being hydrolyzed by proteolytic enzymes. These hydrolysable bonds may be provided within the structure of the molecule itself or alternatively or additionally may be formed when the molecule is labelled by the attachment of a marker.

The term "pathogen" means any infectious agent that can produce disease. Pathogens may comprise, but are limited to, viruses, bacteria, protozoans, prions, viroids, or fungi. Viruses may include, but are not limited to, coronaviruses. Coronaviruses may include, but are not limited to, SARS-CoV-1, SARS-CoV-2, and MERS.

The term "host cells" means any cell that a pathogen can invade directly or indirectly. Direct entry often involves attachment of a pathogen to specific receptors on a host cell and indirect entry may occur through fusion with the host cell membrane.

The term "quencher" means any chemical or biological substance known to those skilled in the art that is capable of absorbing energy, and thus quenching fluorescence from a fluorophore. A quencher may comprise amide bonds, which withdraw electrons from some fluorophores. Fluorophores may comprise, but are not limited to, aminomethyl coumarin (AMC), aminocarbomylcoumarin (ACC), Rhodamine 110, or a combination thereof. Withdrawal of electrons from fluorophores may result in fluorescence quenching in the intact substrate.

The term "crude" means a solution, sample, specimen, cell lysate, or combination thereof that is produced immediately after contact with lysis buffer. A crude solution, sample, specimen, cell lysate, or combination thereof are not subjected to processing steps other than contact with lysis buffer. Processing steps include, but are not limited to, centrifugation, sonification, extraction, separation, or a combination thereof.

The method may provide a simple positive or negative response and/or reading in less than 15 minutes. A positive or negative response and/or reading may be provided in at least about 1 min, about 1 min to about 3 min, about 3 min, to about 5 min, about 5 min to about 7 min, about 7 min to about 9 min, about 9 min to about 11 min, about 11 min to about 13 min, about 13 min to about 15 min, or about 15 min. The method may provide a platform for the detection of various existing and emerging pathogen-mediated disease in humans, animals, and plants.

The method may be used to measure pathogen activity. The signal generated by the method may indicate the presence of natural, therapeutic or vaccine derived antibodies. The presence of antibodies may neutralize the viral activity and reduce the signal. The presence of pathogen activity may also indicate an active infection. The level of pathogen activity may indicate the severity of infection, with greater pathogen activity indicating a greater degree of infection.

The method may comprise a signal generated when a peptide substrate is cleaved by a protease. The signal may be a fluorescence signal that is quenched in an intact substrate by the electron withdrawing properties of an amide bond that connects a C-terminal amino acid with the fluorophore. When the peptide bond between the terminal amino acid and the fluor is cleaved, one peptidic and one nonpeptidic fragment may be produced. The nonpeptidic fragment corresponds to the fluorophore that is now fluorescent. The principle of the electron transfer quenching assay of the present invention for SARS testing is shown in FIG. 1.

The enzyme in the enzyme activity assay, i.e., the protease, may not be consumed in the cleaving process. The enzyme may be available to continue cleaving sites until all enzyme-substrate binding sites have been saturated, effectively amplifying the signal. This process is shown in FIG. 2 by the steady increase of fluorescence over time.

The fluorescent signal may be quenched by a mechanism termed Foerster Resonant Energy Transfer (FRET). In FRET, photons emitted by a fluorophore upon excitation by a light source (e.g., mercury lamp, laser, or LED) are absorbed by a quencher that "turns off" fluorescence. Energy transfer from the fluorophore to the quencher may be highly distance dependent and occurs only up to a distance of approximately 10 nm (corresponding to approximately 28 amino acids). Therefore, when a FRET peptide is cleaved by a protease, fluorescence is "turned on" as the quencher and fluorophore move apart. The principle of a FRET assay of the present invention that may be used as an internal control for SARS testing is shown in FIG. 3. The FRET peptide may be recognized by human angiotensin converting enzyme 2 (ACE2) that is ubiquitously expressed on epithelial cells in the oral cavity through which SARS coronaviruses and other viruses enter cells. The control confirms that the sample collected has sufficient quantity and quality for the method to perform properly. As an example of the function of the internal control, a fluorescence increase of ACE2 substrate as a function of the lysate concentration is shown in FIG. 4.

The method may comprise using a substrate. Substrates are generally specific for one enzyme. Substrates may comprise but are not limited to, DNA, RNA, protein, peptides, or a combination thereof. The peptide may correspond to the amino acid sequence of a pathogen protein. Substrates may comprise a signaling moiety. The signaling moiety may be attached to the substrate. Moiety attachment may be by conjugation. The signaling moiety may produce a fluorescent, colorimetric, or chemiluminescent signal. The substrate may comprise a gene fragment, ubiquitin, amino acids, or a combination thereof. The substrate may comprise one or more biological fragments. The biological fragments may comprise gene fragments, ubiquitin fragments, or a combination thereof. The gene may comprise ISG15. The substrate may comprise ubiquitin. Ubiquitin may be attached to the substrate. The ubiquitin may be attached by conjugation. The ubiquitin may be naturally attached to the substrate. Substrates with unnatural amino acids may be used to confer specificity for an enzyme and may be added to fragments of ubiquitin and ISG15 separately or as a conjugate.

The substrate may be cleaved by a protease. The protease may be a pathogen protease. For example, substrates that are cleaved by coronavirus papain-like proteases are based on the amino acid sequence motif R-L-X-G-G (SEQ ID NO. 4). The substrate may comprise the amino acid sequence R-L-X-G-G (SEQ ID NO. 4), L-R-G-G (SEQ ID NO. 1), or a combination thereof. Ubiquitin and ISG15 with a terminal L-R-G-G (SEQ ID NO. 1) sequence may be added in a competitive assay where the substrate is a labeled tetrapeptide based on the L-R-G-G (SEQ ID NO. 1) sequence. Ubiquitin and ISG15 without the C-terminal L-R-G-G (SEQ ID NO. 1) sequence may be generated and added separately to a tetrapeptide based on the L-R-G-G (SEQ ID NO. 1) sequence. Ubiquitin and ISG15 substrates without the C-terminal L-R-G-G (SEQ ID NO. 1) sequence may be added in several fragments and added separately to a tetrapeptide based on the L-R-G-G (SEQ ID NO. 1) sequence.

Substrates may be derived from different species to identify a pathogen. Substrates may be preferentially cleaved by a pathogen depending on the species the substrate sequence is derived from. For example, SARS-CoV-1 does not cleave ISG15 from fish or camel, whereas SARS-CoV-2 cleaves ISG15 from fish and MERS cleaves ISG15 from camel. Thus, substrates from different species may identify specific pathogens including, but not limited to, coronaviruses.

Screening combinatorial substrate libraries containing a wide variety of nonproteinogenic amino acids allows to further define substrates that are recognized only by one protease and not by another within a family. For example, peptides may be specifically cleaved by SARS PLpro but not by MERS PLpro or human deubiquitylating enzymes. Peptides specifically cleaved by SARS PLpro have the following sequences: Ac-Abu(Bth)-Dap-G-G, Ac-hTyr-Phe(guan)-G-G, Ac-Tyr-Dap-G-G, and Ac-hPhe-Dap-G-G. Ubiquitin and Interferon Stimulated Gene15 are other substrates that are recognized by papain-like proteases and cleaved at their carboxyterminal L-X-G-G amino acid sequence.

Modifications to substrates affected by enzymes may comprise, but are not limited to, phosphorylation, dephosphorylation, methylation, demethylation, ubiquitinylation, deubiquitylation, glycosylation, acetylation, hydroxylation, addition, and removal of Interferon Stimulating Gene 15 (ISG15), or a combination thereof. Enzymes may also affect cleavage of their substrates.

The method may detect any pathogen variant. False-negative test results from "variants" with mutations in enzyme active sites are exceedingly unlikely to occur because enzyme active site mutations would reduce or abolish pathogen function and are not compatible with survival and/or transmission. In contrast, variants with mutations in other regions of the viral genome that do not interfere with enzyme active sites will not affect the ability of a test to detect pathogens.

The method may directly measure the efficacy of natural, therapeutic, or vaccine-derived antibodies by detecting the activity of enzymes from pathogens that were able to enter a host cell. Therefore, the method of the present invention may be used as a portable companion diagnostics test. Subjects enrolled in pharmaceutical clinical trials that test the efficacy of therapeutic or vaccines-derived antibodies may be given a complete test system and report daily test results directly to the clinical trial center, for example, by a mobile phone and/or mobile phone application.

The method may accelerate cell-based drug discovery by measuring the potencies of inhibitors against natural, unmodified enzyme. The present invention may be applied to screen peptide libraries using crude active lysates from cultured cells to quickly and efficiently identify peptides that are cleaved by the enzyme of interest with the least cleavage from endogenous host enzymes.

The method may comprise using an enzymatic assay. The enzymatic assay may comprise a fluorescence-based assay system using a substrate labeled with a quencher and a fluorophore which together form a Foerster (or Fluorescence) Resonance Energy Transfer (FRET) pair. The emission may be quenched by the quencher in an intact substrate and liberated upon cleavage. Fluorophores, may comprise, but are not limited to, amino-methylcoumarin (AMC), amino carbomylcoumarin (ACC), Rhodamine 110, or a combination thereof. Fluorophores may be quenched by the electron withdrawing properties of the amide bond between the terminal amino acid and the fluorophore of the substrate. Fluorophores may not require a separate quencher to be quenched.

Formats for performing enzymatic assays may comprise, but are not limited to, wells of multi-well plates, vials, cuvettes, microscope slides, test strips, or a combination thereof. The fluorescence liberated after cleavage may be detected in any device capable of providing excitation light, e.g., an LED, mercury lamp, or laser, and recording emission. These devices may comprise, but are not limited to, battery-operated handheld fluorometers containing LEDs and appropriate photodiodes, benchtop plate-based fluorometers, fluorescence activated cell sorters (FACS), fluorescence microscopes, real time polymerase chain reaction (RT-PCR) machines, quantitative real time polymerase chain reaction (Q-PCR), or a combination thereof.

The enzymatic assay may comprise a membrane permeable enzyme reporter substrate. The enzyme reporter substrate may be labeled with a reagent, including but not limited to, Rhodamine 110. The enzyme reporter substrate may be added directly to live cells. The enzyme reporter substrate may enter cells and may be cleaved by endogenous enzymes. Cleavage may be observed in real time by monitoring the fluorescence increase in a fluorescence microscope, fluorometer, or any other device capable of detecting fluorescence.

Cleavage of substrates may also be detected using lateral flow assays (LFA) where portions of substrates are captured on the matrix by immobilized capture reagents. The Capture reagent may comprise, but is not limited to, streptavidin, antibodies, or a combination thereof. Captured substrate portions, i.e., captured analytes, may be detected using detection antibodies with conjugated chromogens, metal particles, or a combination thereof.

The enzymatic assay may comprise a chromatography technique. The chromatography technique may comprise, but is not limited to, size exclusion chromatography, gel-based separation, fluorescence polarization, or a combination thereof to detect the change in the size of the reporter substrate. The enzymatic may also comprise substrates labeled with an electrochemically active label that records cleavage activity.

The enzymatic assays may be homogeneous or heterogeneous. Homogeneous enzymatic assays may be of the add-and-mix type. Heterogeneous enzymatic assays may comprise steps including, but not limited to, precipitation and/or separation. In homogeneous enzymatic assays, the progress of a reaction may be monitored in real time as the reaction occurs or at the beginning and end of the reaction. Enzymatic assays may measure the activity of enzymes of a pathogen or an infectious agent capable of inducing a selective alteration in enzyme activity in the host.

The method may comprise a fluorescent dye. The fluorescent dye may act as a fluorophore. The excitation and emission properties of the fluorophore may fall within any measurable wavelength range, for example, an absorption range between 300 nm to 800 nm and emission range, for example, between 350 nm to 800 nm. The fluorescent dye may fall into various classes, where combinations of fluorescent dyes may be used in the same class or between different classes. The classes of the fluorescent dye may comprise, but are not limited to, xanthene dyes, e.g., fluoresceins and rhodamines; coumarins, e.g., umbelliferone; benzimide dyes, e.g., Hoechst 33258, phenanthridine dyes e.g., Texas Red and ethidium dyes; acridine dyes; Bodipy; cyanine dyes, e.g., thiazole orange, thiazole blue, Cy 5, and Cyfr; carbazole dyes; phenoxazine dyes; porphyrin dyes; quinoline dyes; or a combination thereof. The fluorescent dye may absorb light in the ultraviolet, visible, or infrared wavelength ranges or a combination thereof.

The method may comprise an organic dye. Organic dyes may be used as quenchers in FRET assays if the organic dye is spectrally matched with the fluorophore. The method may also comprise a quencher. Quenchers may be fluorescent themselves or be dark quenchers with little or no intrinsic fluorescence. Dark quenchers may comprise, but are not limited to, 4-(4'dimethylaminophenylazo)benzoic acid (DABCYL). Quenchers may comprise black hole quenchers. Black hole quencher may comprise diazo dyes of the BHQ series. Black hole quenchers may provide a broad range of absorption which overlaps well with the emission of many fluorophores. Quenchers may be directly bonded to the substrate. Quenchers may be bonded indirectly to substrate, for example, by metal-ion association to a phosphate group present on the substrate. Metal ions capable of bonding to phosphate-labeled substrates and quenching the fluorescence of a reporter fluorophore may comprise, but are not limited to, divalent and/or trivalent metal ions. The divalent and trivalent metal ions may comprise, but are not limited to, iron, gallium, zirconyl chloride, manganese chloride, or a combination thereof.

Figure 5:
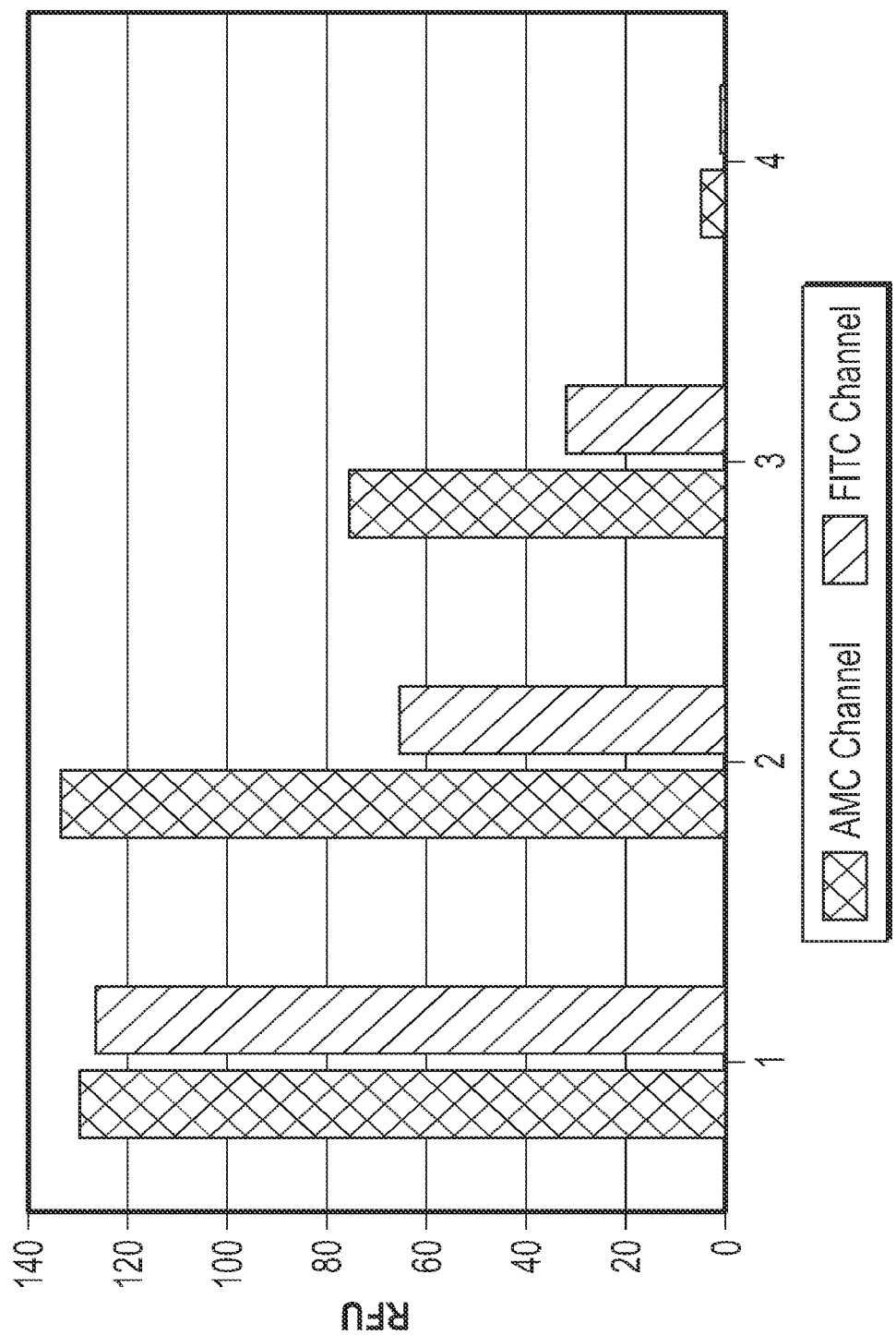
FIG. 5 is a graph showing the simultaneous measurement of peptides upon cleavage by endogenous ACE2 and recombinant PLpro.

Peptides cleaved by PLpro and ACE2 may be labeled with different fluorophores that have non-overlapping excitation and emission properties. This allows both peptides to be measured simultaneously in one sample, as shown in FIG. 5.

The method may comprise a specimen. The specimen may comprise, but is not limited to, a tongue scrape, saliva, sputum, blood, urine, nasal and anal swabs, mucus, serum, plasma, urine, spinal fluid, tissue biopsy, vaginal fluid, amniocentesis fluid, tears, bronchoalveolar fluid, other fluid or tissue or cells, or a combination thereof. The specimen may comprise any cell type. The specimen may also comprise crude lysates from cells that are grown in culture. Crude lysates from cells that are grown in culture were used in the experiment results shown in FIG. 13, FIG. 15, and FIG. 16.

Tongue scrape specimen samples may comprise an enrichment of cellular, potentially virus-infected material in cells from the tongue. Hundreds of viruses may be present in each infected cell, and around 30 million cells/cm$^2$ are collected in a tongue scrape. Lysate derived from a specimen may be used directly without any further processing, e.g., filtration, or centrifugation. Crude cell lysate may be stable for at least about 2 hours, about 2 hours to about 4 hours, about 4 hours to about 6 hours, about 6 hours to about 8 hours, about 8 hours to about 10 hours, about 10 hours to about 12 hours, or about 12 hours on ice. Cell lysate may be stable for at least about 2 days, about 2 days, to about 5 days, about 5 days to about 10 days, about 10 days to about 15 days, about 15 days to about 20 days, about 20 days to about 25 days, about 25 days to about 30 days, or about 30 days when frozen at about −20° C. to about −80° C.

The method may comprise using a kit for detecting protease activity in crude lysates from cells. The kit may comprise a specimen collector. The specimen collector may comprise a tongue scraper, a transfer pipette, a collection vial comprising lysis buffer, a vial comprising assay components in liquid or freeze-dried form, or a combination thereof. Optionally, the assay components may be in a form to remain active without specialized storage conditions.

The method may comprise a multiplex test to detect PLpro and ACE2 simultaneously. The multiplex test may be used in combination with a fluorometer. The fluorometer may be a commercial fluorometer and may be battery-operated and/or handheld. The multiplex test may comprise collecting a specimen and at least partially disposing the specimen in a specimen vial. The specimen may be a tongue scrape. The specimen vial may comprise a lysis buffer that disrupts the lipid membrane of cells and viruses. A solution may be formed by contacting the specimen with the lysis buffer. The solution may be transferred to a vial that contains all components for the test in a stable form. The vial may be at least partially disposed within a fluorometer. The fluorometer may be configured to measure emission from the positive control ACE2 peptide and the second to measure emission from the PLpro peptide. The channels may be switched by the push of a button.

The method may comprise test reagents and sampling materials sufficient for a single measurement. Alternatively, the method may comprise enough reagents for hundreds to thousands of measurements. Measurements may be performed in multi-well plates, including but not limited to, 96-well, 384-well, and/or 1536-well plates for high content screening (HCS) and/or high throughput screening (HTS) applications.

Figure 8:
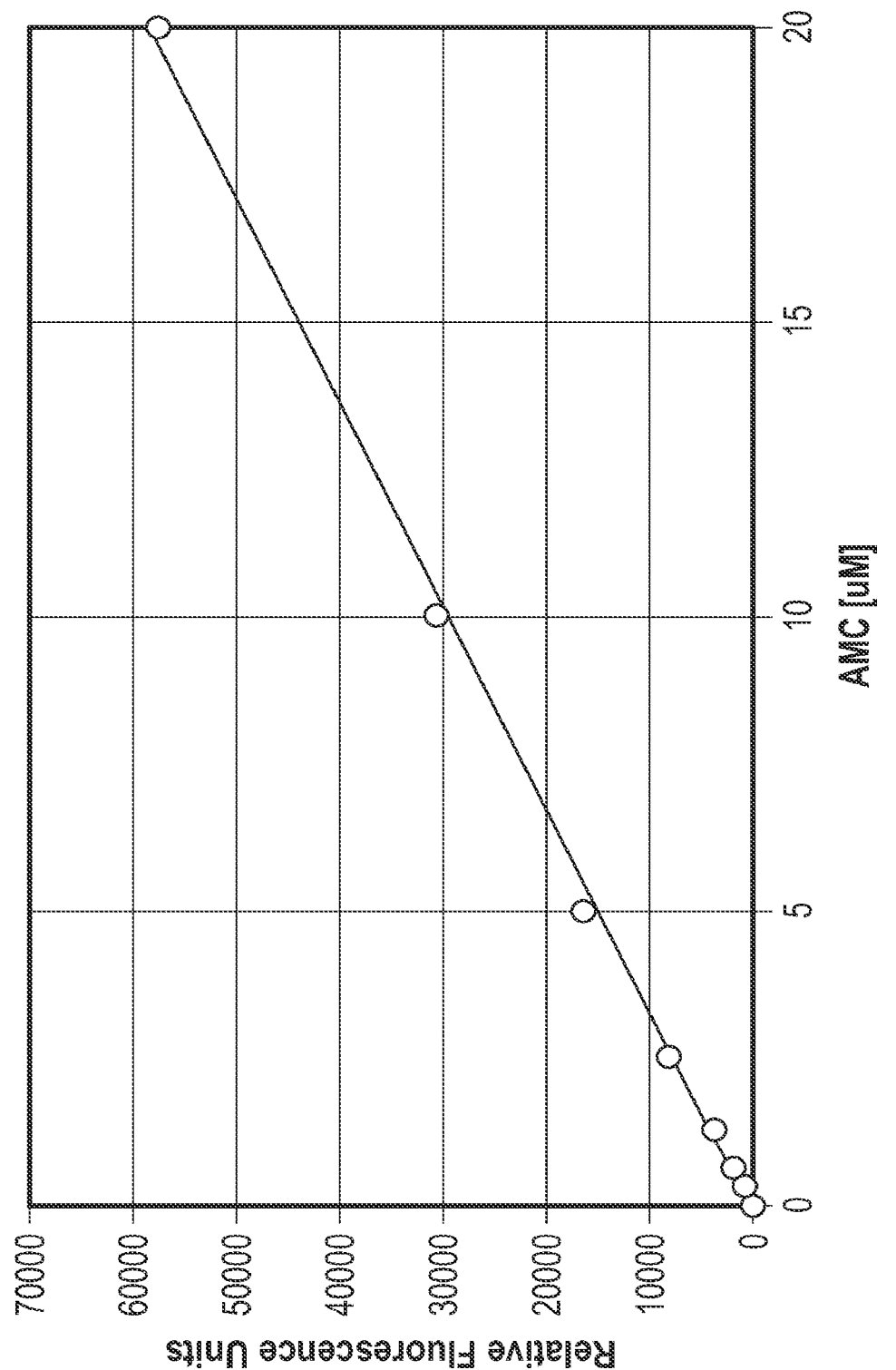
FIG. 8 is a graph showing serial dilutions of unconjugated 7-amino-methylcoumarin (AMC)

Optionally, the method may comprise a calibrator. The calibrator may allow for semi-quantitative determination of the viral load. The calibrator may comprise serial dilutions of unconjugated and unquenched fluorophore. As an example, FIG. 8 shows a linear calibrator response that is 50% broader than the expected response from samples.

The quantity of specimen may be normalized to the measured signal measured allowing for the quantification of the pathogen load. For example, total protein can be rapidly measured in solution by the interaction of a fluorophore with the amines of polypeptides. Three readings of each sample may be taken, including the fluorescence derived from PLpro peptide cleavage; the fluorescence derived from ACE2 peptide cleavage; and the fluorescence of an amine-binding protein quantifying dye added to the sample after the enzymatic reactions are completed. Other reagents can be used to quantify the specimen lysate. These other reagents may comprise, but are not limited to, reagents that measure DNA, e.g., with Hoechst Dye 33258, RNA, any other common biological in crude lysate, or a combination thereof.

The fluorescence from samples may be taken immediately and thereafter at regular or semi-regular intervals. Typical interval periods may be at least about 30 sec, about 30 sec to about 1 min, about 1 min to about 2.5 min, about 2.5 min to about 5 min, about 5 min to about 10 min, about 10 min to about 15 min, or about 15 min. The difference in relative fluorescence units (RFU) between the time 0 reading and the final endpoint may be calculated (delta RFU).

A large delta RFU from the PLpro peptide may indicate the presence of a pathogen and a large delta RFU from the ACE2 peptide, the internal positive control, may indicate successful sampling, lysis, and assay performance. Delta RFU from the ACE2 peptide only indicates the absence of pathogen infection, and absence of delta RFU from the ACE2 peptide indicates an inconclusive test.

The method may be an activity-based diagnostics approach intended for semi-quantitative and/or quantitative detection of SARS PLpro activity in crude lysates collected from cells in the oral cavity. The method may be used to test individuals suspected of having COVID-19 or for use in individuals without symptoms or other epidemiological reasons to suspect COVID-19, using supervised or unsupervised sample collection. Testing may be performed at point of care (POC) sites or in patient care settings operating under a Clinical Laboratory Improvement Amendments of 1988 (CLIA) certificate or at sites that can perform low complexity tests approved for waiver under the Clinical Laboratory Improvement Amendments of 1988 (CLIA). CLIA-certified sites may include laboratories, hospitals, or any other centralized testing site. CLIA-waived sites may include pharmacies, doctor's offices, border control agencies, airports, schools, colleges, businesses, or personal residences.

The method may comprise using any device capable of fluorescence excitation and emission measurement suitable as the measurement device of the current invention. The device may comprise, but is not limited to, a battery-operated instrument, a handheld instrument, a benchtop plate-based fluorometer, a fluorescence activated cell sorter (FACS), a fluorescence microscope, an RT-PCR machine, a Q-PCR machine, or combination thereof. Testing using fluorescence microscopes may comprise deposition of specimens into well-based microscope slides. Testing using RT-PCR machines may comprise programming the instrument to cycle at one temperature, e.g., at about room temperature.

Figure 9:
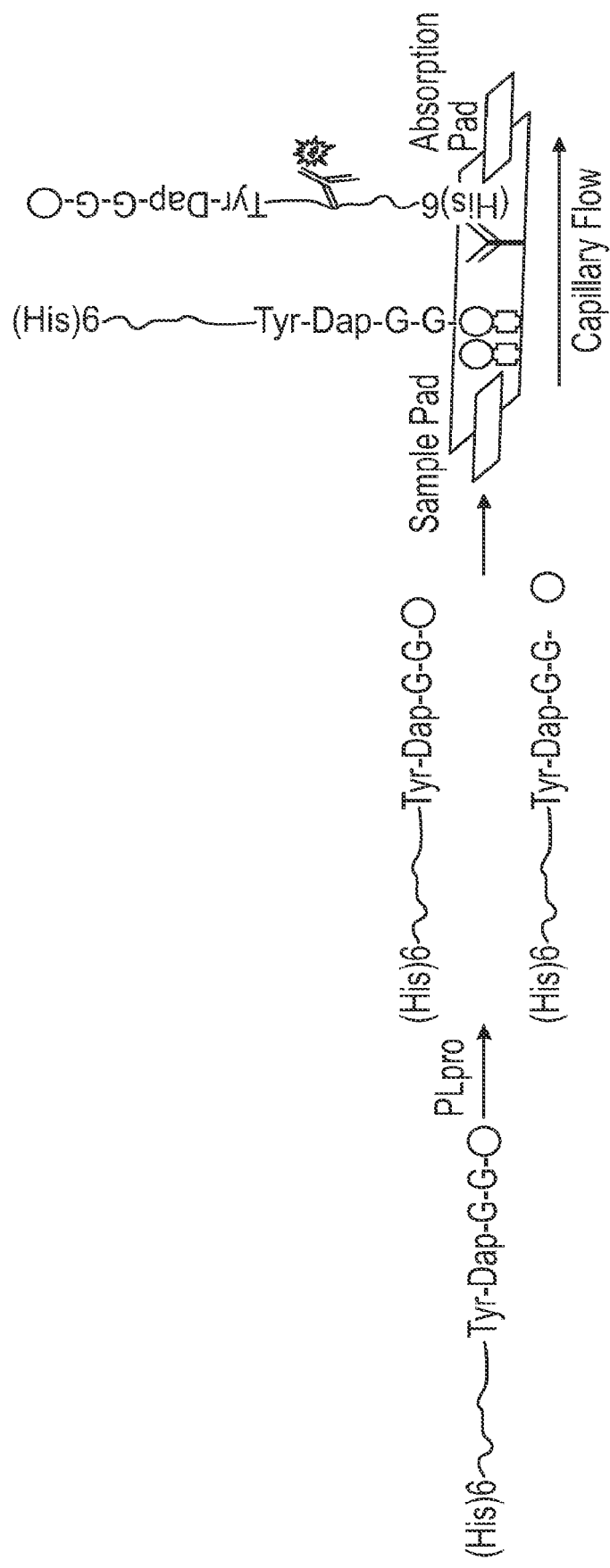
FIG. 9 is a schematic of a lateral flow assay based on the SARS protease cleavage assay.

The method may comprise a lateral flow assay (LFA). Activity-based diagnostics approach may be used for detection of cleavage using LFAs. In this application, biotinylated substrates and fragments may be captured on the matrix by immobilized capture reagents. The reagents may comprise streptavidin. The cleaved fragment may be detected using detection antibodies that are labeled with chromogens or metal particles. An example of cleaved fragment detection using avidin and antibodies is shown in FIG. 9.

The method may comprise using a viral enzyme as a biomarker of a pathogen. Viral enzymes are essential for survival and "variants" that lead to loss of function are not viable. These viral enzymes may naturally be present in cell lysate. Therefore, enzyme-activity based tests have reduced false-negative results due to variants compared to other methods. Enzyme-activity based tests provide a generic platform for detecting known and new variants that may evade detection by other methods such as RT-PCR and escape immunity from neutralizing antibodies.

Figure 10:
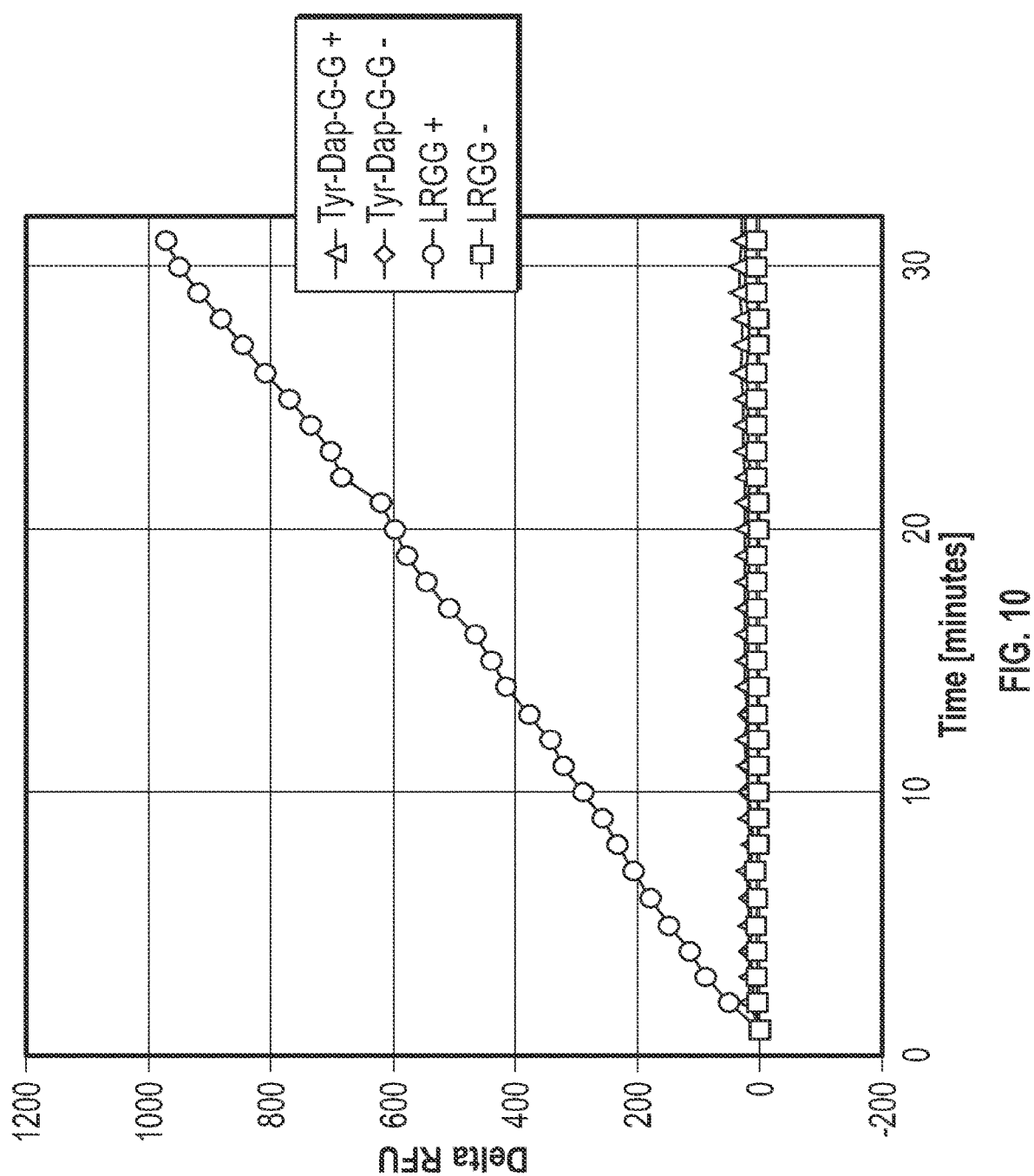
FIG. 10 is a graph showing cleavage of peptides with the amino acid sequence L-R-G-G-AMC (SEQ ID NO. 5) or Tyr-Dap-G-G-AMC in the presence (+) or absence (−) of crude tongue scrape lysate.
Figure 15:
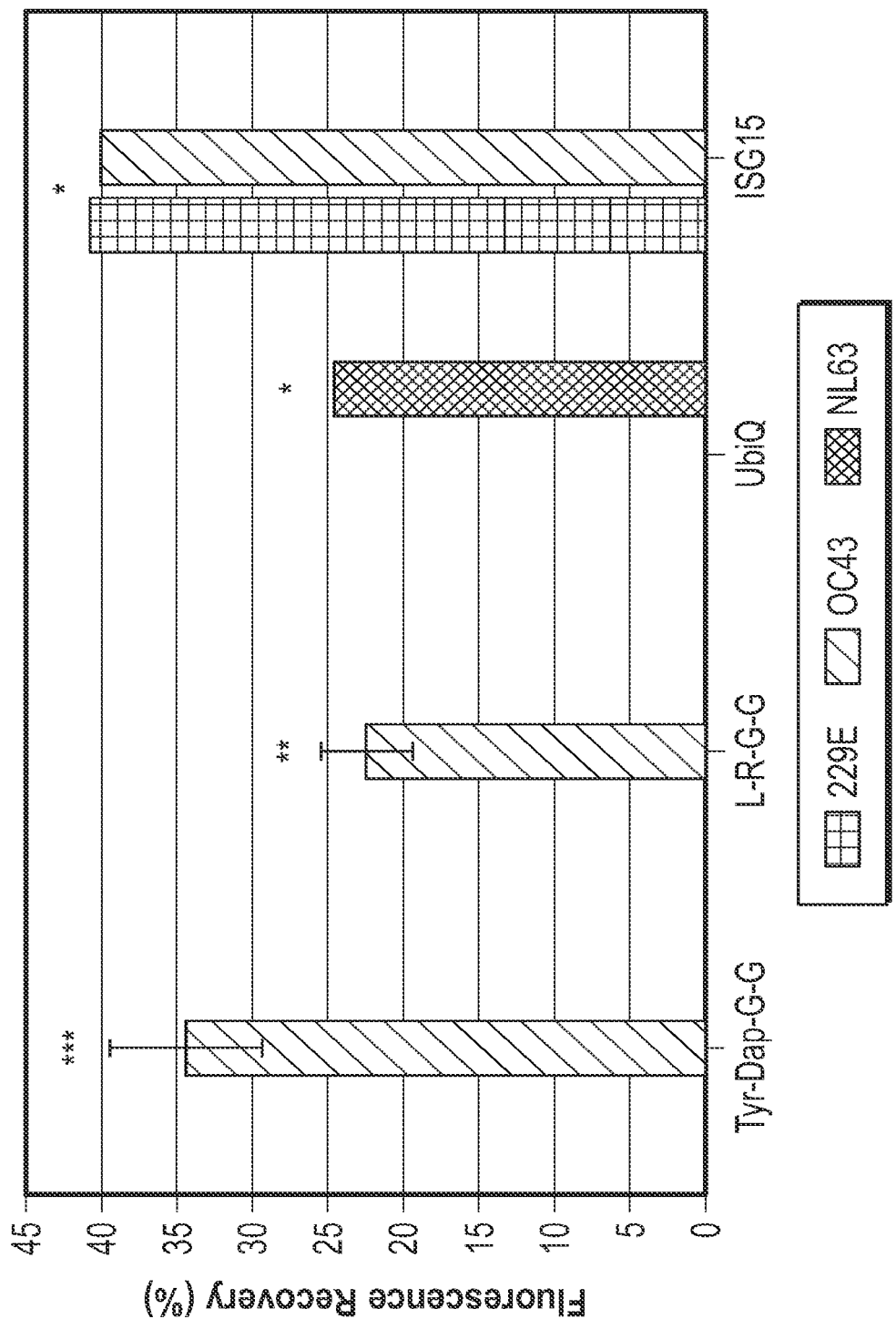
FIG. 15 is a graph showing the cleavage of substrates Tyr-Dap-G-G, L-R-G-G (SEQ ID NO. 1), ubiquitin (UbiQ) and ISG15 in crude lysates from infected human cells.

The method may be specific to a certain substrate. For example, MERS PLpro and human UCH-L3 do not recognize the substrate hTyr-Dap-G-G used in the present invention to measure SARS PLpro activity and this was confirmed using crude tongue scrape lysate as shown by FIG. 10; or using crude lysates from cells infected with coronavirus 229E, as shown in FIG. 15. Although tetrapeptides may be converted in crude lysates from cells infected with 0043 coronavirus, the cleavage was observable only after 60 or 800 minutes.

ISG15 and/or ubiquitin binding in the SARS PLpro substrate binding site may be distant from the active site where the L-R-G-G-based peptide (SEQ ID NO. 1) is bound. The method may combine the sensitivity-conferring ISG15 and/or ubiquitin protein (without the tetrapeptide cleavage sequence) and the specificity-conferring readout peptide Tyr-Dap-G-G-AMC (where AMC=aminomethyl coumarin) to obtain a substrate mixture that confers superior sensitivity and specificity to SARS PLpro. For example, the ISG15 and/or ubiquitin peptide without the terminal L-R-G-G (SEQ ID NO. 1) sequence may be combined with the substrate Tyr-Dap-G-G-AMC to SARS coronavirus PLpro before, later, or at the same time. More than two fragments of a specific substrate may also be added. Optionally, one substrate may be produced that comprises the ISG15 and/or ubiquitin sequence and the specificity-conferring sequence.

The method may be used to determine optimal cleavage using ISG15 and ubiquitin substrates from different species. Monitoring the slopes of reaction progress over time gives an estimate of the catalytic rates, which may provide a further differentiator between the pathogens, i.e., viruses, bacteria, and/or coronaviruses, to identify them. For example, PLpro from SARS-CoV-1, SARS-CoV-2 and MERS all cleave tetrapeptide, ubiquitin, and ISG15 but at substantially different rates. The differences in catalytic conversion of ubiquitin and ISG15 between SARS-CoV-1 and SARS-CoV-2 are expected to allow distinguishing between the SARS strains.

Quantification of ACE2 measurement may be predictive of the risk for becoming infected with SARS viruses as these coronaviruses enter cells through ACE2. A high expression may be indicative of a higher risk for infection than a low expression. Quantification is achieved by determining the protein amount present in the sample and calculating the amount of protein relative to the activity of ACE2. In addition, upregulation of ACE2 might be an independent marker of SARS infection. The enzymatic assay results in FIG. 16 show that ACE2 is an independent marker of SARS infection in in vivo studies using human tissue cultured cells infected with coronavirus 229E.

The method may comprise using a rapid cell lysis protocol with which cells from human tongue scrape are immediately lysed. The rapid cell lysis protocol may comprise using lysis buffer. The lysis buffer may keep enzymes in the active form and enzyme activity may be measured for at least about 2 hours, about 2 hours to about 4 hours, about 4 hours to about 6 hours, about 6 hours to about 8 hours, or about 8 hours after sampling. Rapid refers to a period less than about 10 min, about 10 min to about 9 min, about 9 min to about 8 min, about 8 min to about 7 min, 7 min to about 6 min, about 6 min to about 5 min, about 5 min to about 4 min, about 4 min to about 3 min, about 3 min to about 2 min, about 2 min to about 1 min, or about 1 min.

The method may comprise detergents. The detergents may comprise, but are not limited to, other detergents, such as Triton X-100, Triton X-114, Igepal® CA-630, n-dodecyl-β-D-maltoside (DDM), beta-decyl-maltoside, octyl-glucoside, digitonin, polysorbate 20, polyoxyethylene sorbitan monolaurate, PEG (20) sorbitan monolaurate, polysorbate 80, polyoxyethylene sorbitan monooleate, PEG (80) sorbitan monooleate, glyco-lithocholate amphiphiles (GLC-1, GLC-2, and GLC-3), glyco-diosgenin amphiphile (GDN), 3-[(3-cholamidopropyl)dimethylammonio]-1-propanesulfonate (CHAPS), or a combination thereof. The detergents may comprise non-ionic detergents. The non-ionic detergents may comprise uncharged hydrophilic headgroups. The non-ionic detergents may be mild surfactants capable of breaking protein-lipid and lipid-lipid associations, but not protein-protein interactions. The non-ionic detergents may not be capable of denaturing proteins. The method may comprise using a solvent for detergents. The solvent may comprise, but is not limited to, phosphate buffered saline (PBS), tris(hydroxymethyl)aminomethane (TRIS), (4-(2-hydroxyethyl)-1-piperazineethanesulfonic acid (HEPES), 2-ethanesulfonic acid (MES), any other biological buffer, any non-biological buffer, or a combination thereof.

The method may comprise using inhibitors of phosphatases, kinases, or proteases. Phosphatases, kinases, proteases, and other enzymes present in the lysate may alter the activity of the enzyme of interest and an inhibitor may be used to inhibit the activity of unwanted enzyme activity. Inhibitors of phosphatases, kinases, or proteases may be added to the lysis solution. Inhibitors may inhibit proteases, including, but not limited to, trypsin, chymotrypsin, and elastase; cysteine proteases, including but not limited to, papain, calpain and lysosomal cathepsins; aspartic proteases, including but not limited to, pepsin and rennin; and metallo-proteases, including but not limited to, thermolysin and carboxypeptidase A. Inhibitors may be present as individual compounds or as mixtures.

The method may measure enzyme activity in host cells infected with pathogens that were able to evade the neutralizing activity of an antibody or other blocking agent. Cleavage may be monitored in intact cells or in lysates from cells that were pretreated with antibody and transfected with the substrate. The biomarker within the method may be an enzyme, e.g., PLpro, that is produced only by live virus in infected cells.

The method may be used in high-throughput screens. In high-throughput screens, large numbers of single measurements of unknown samples are compared to positive and negative control samples. Prior to starting a large screen, smaller test screens are used to assess the quality of an assay. The Z' factor is used as a statistical measure that predicts the suitability of an assay for screening. Z' takes into account 4 parameters: the means (p) and the standard deviations (G) of the positive and the negative control. The controls are equivalent to the upper and lower limit of the assay. The Z' factor is calculated according to the following equation:

$$Z' = 1 - \frac{3\sigma\text{max} - 3\sigma\text{min}}{\mu\text{max} - \mu\text{min}}.$$

A Z' of >0.5 indicates that an assay has good performance for drug screening. The method may generate Z factors between approximately 0.7 to 0.84 at various enzyme concentrations.

PLpro, is an essential enzyme that has multiple roles: it cleaves the viral polyprotein and has ubiquitin and interferon-stimulated gene 15 (ISG15) cleaving activities. The multiple roles of PLpro and the high conservation of its active sites make PLpro an excellent therapeutic target for small molecule libraries Turning now to the drawings, FIG. 1 shows a schematic representation of a quench mechanism based on electron transfer. A synthetic peptide comprising four amino acids (circles) is labeled with the fluorophore AMC. In the intact peptide, the fluorescence from the fluorophore is quenched by the amide bond between the terminal amino acid of the peptide. When the peptide is cleaved by PLpro, one peptidic and one non-peptidic fragment is produced. The emission is monitored at 465 nm with excitation at 365 nm.

Figure 2:
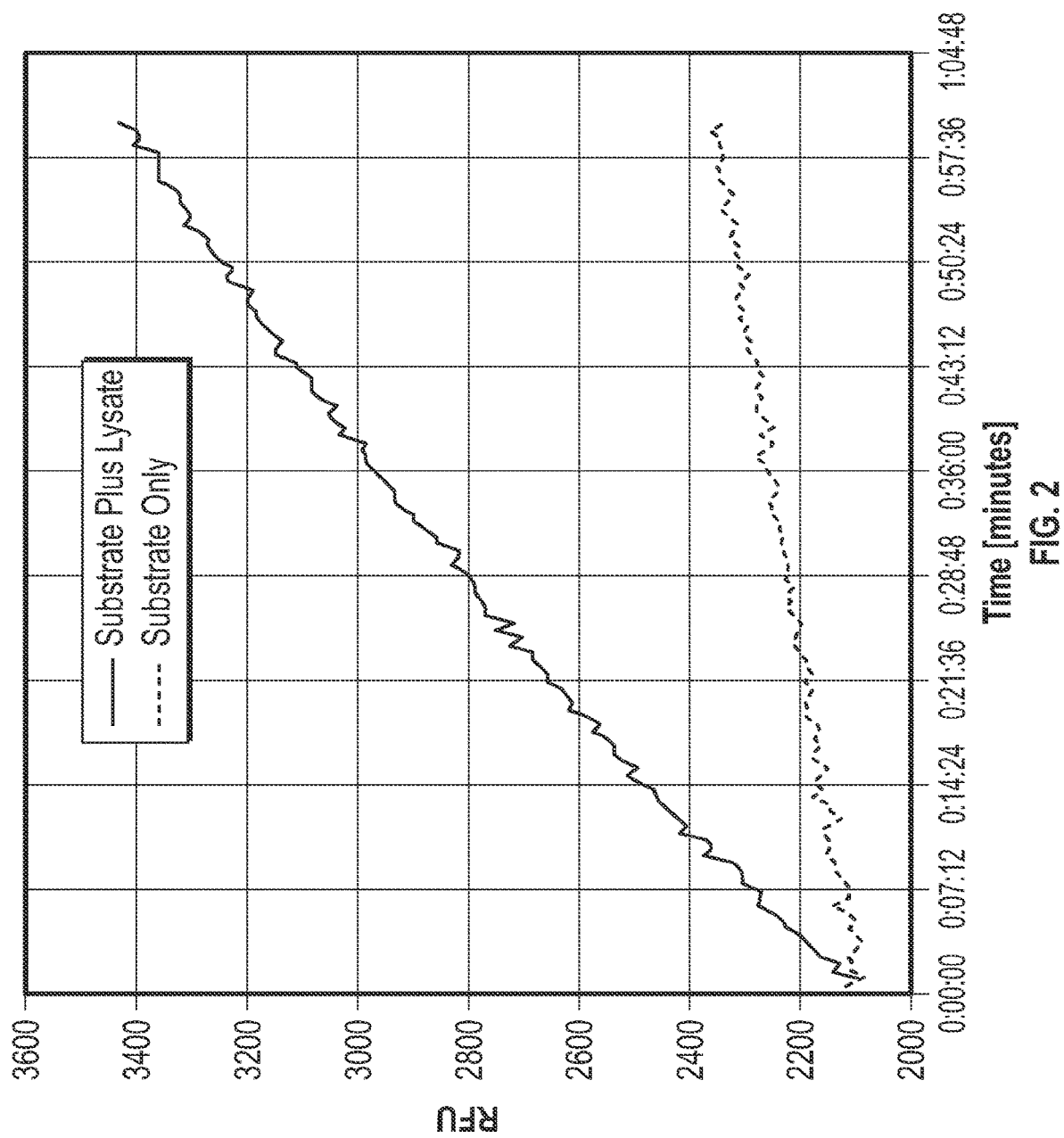
FIG. 2 is a graph showing a fluorescence increase through cleavage of the electron transfer substrate in crude tongue scrape lysate to which recombinant PLpro was added.

FIG. 2 is a progress curve showing a fluorescence increase through cleavage of the electron transfer substrate from FIG. 1 in crude tongue scrape lysate to which recombinant PLpro was added. The control reaction does not contain recombinant PLpro.

Figure 3:
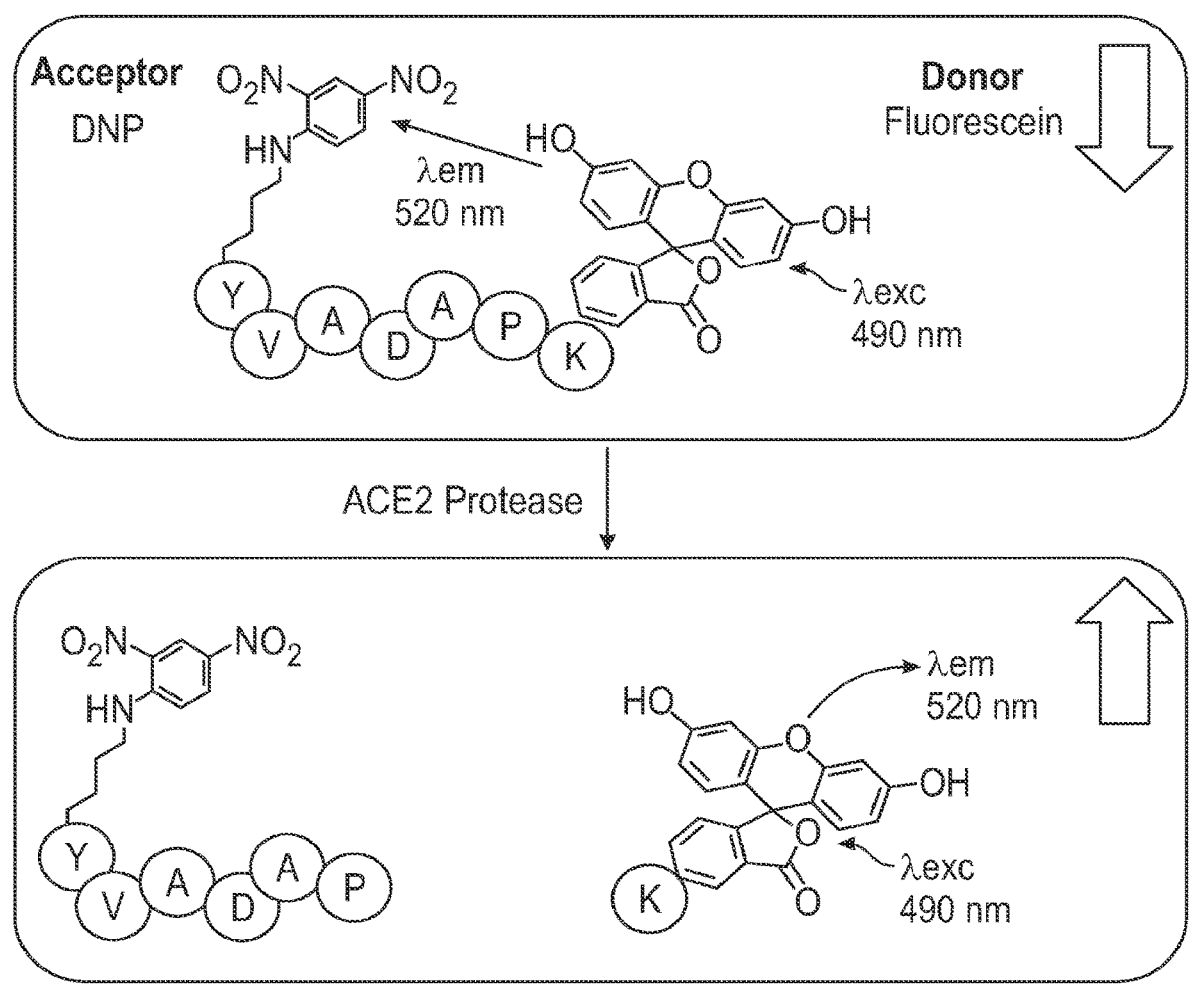
FIG. 3 is a schematic showing of a quench mechanism based on Foerster Resonance Energy Transfer (FRET), where a peptide composed of seven amino acids (circles) (SEQ ID NO. 2) is labeled on one end with the fluorophore fluorescein isocyanate and on the other with a quencher dinitrophenyl (DNP)

FIG. 3 shows a schematic representation of a quench mechanism based on Foerster Resonance Energy Transfer (FRET). A peptide comprising seven amino acids (circles) is labeled on one end with the fluorophore fluorescein isocyanate and on the other with a quencher dinitrophenyl (DNP). When the peptide is excited using a wavelength of 490 nm, energy is transferred from the acceptor (fluorescein) to the donor. Upon cleavage, the donor and acceptor move apart and emission from the acceptor can be monitored at 520 nm.

Figure 4:
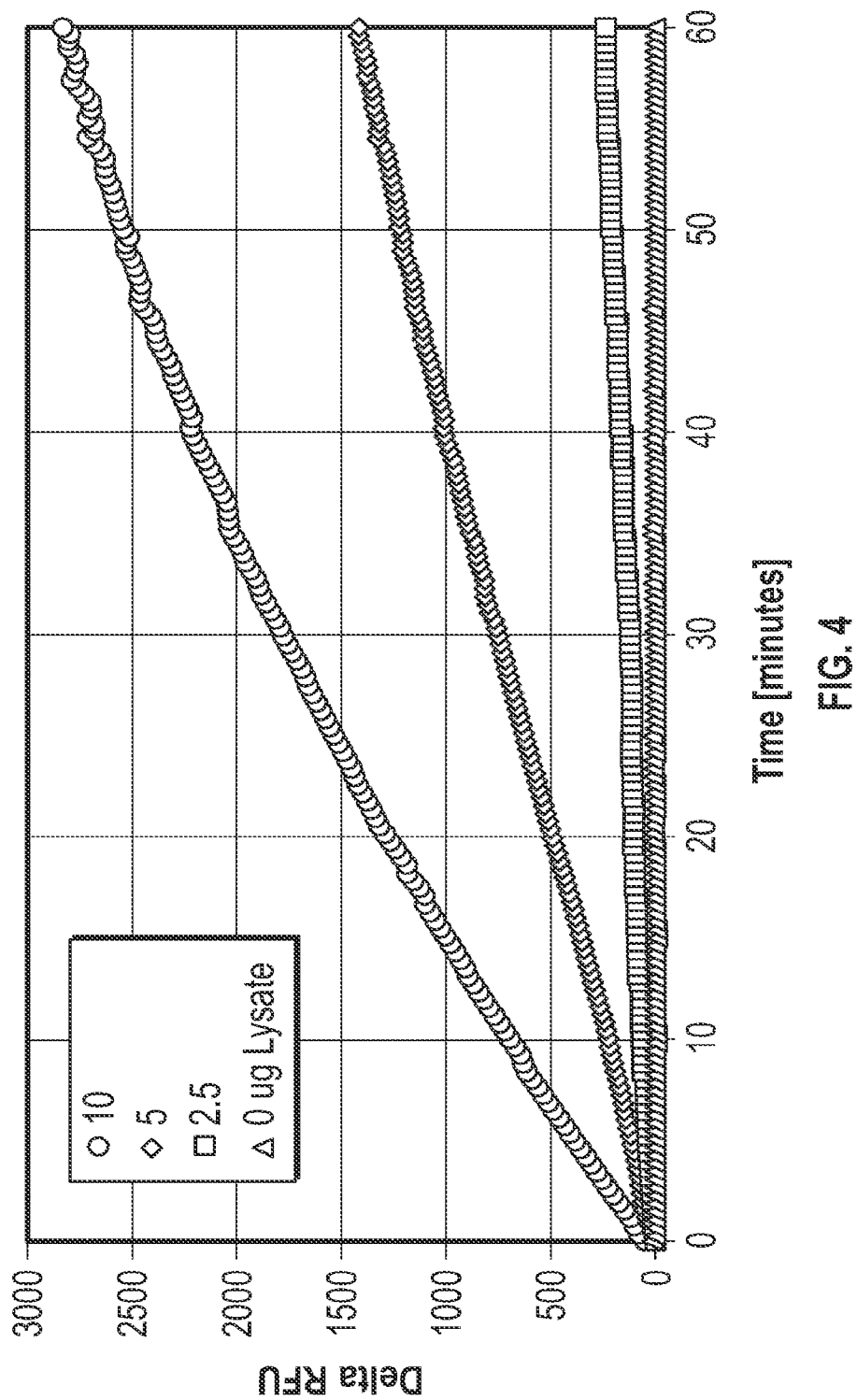
FIG. 4 is a graph showing fluorescence increase through cleavage of the FRET substrate.

FIG. 4 is a progress curve showing fluorescence increase through cleavage of the FRET substrate from FIG. 3 by endogenous enzymes in three dilutions of crude lysate from tongue scrapes. FIG. 5 shows a multiplexed measurement of the peptides from FIG. 1 and FIG. 3 upon cleavage by endogenous ACE2 and recombinant PLpro. The fluorescence is measured in a battery-operated handheld fluorometer.

Figure 6:
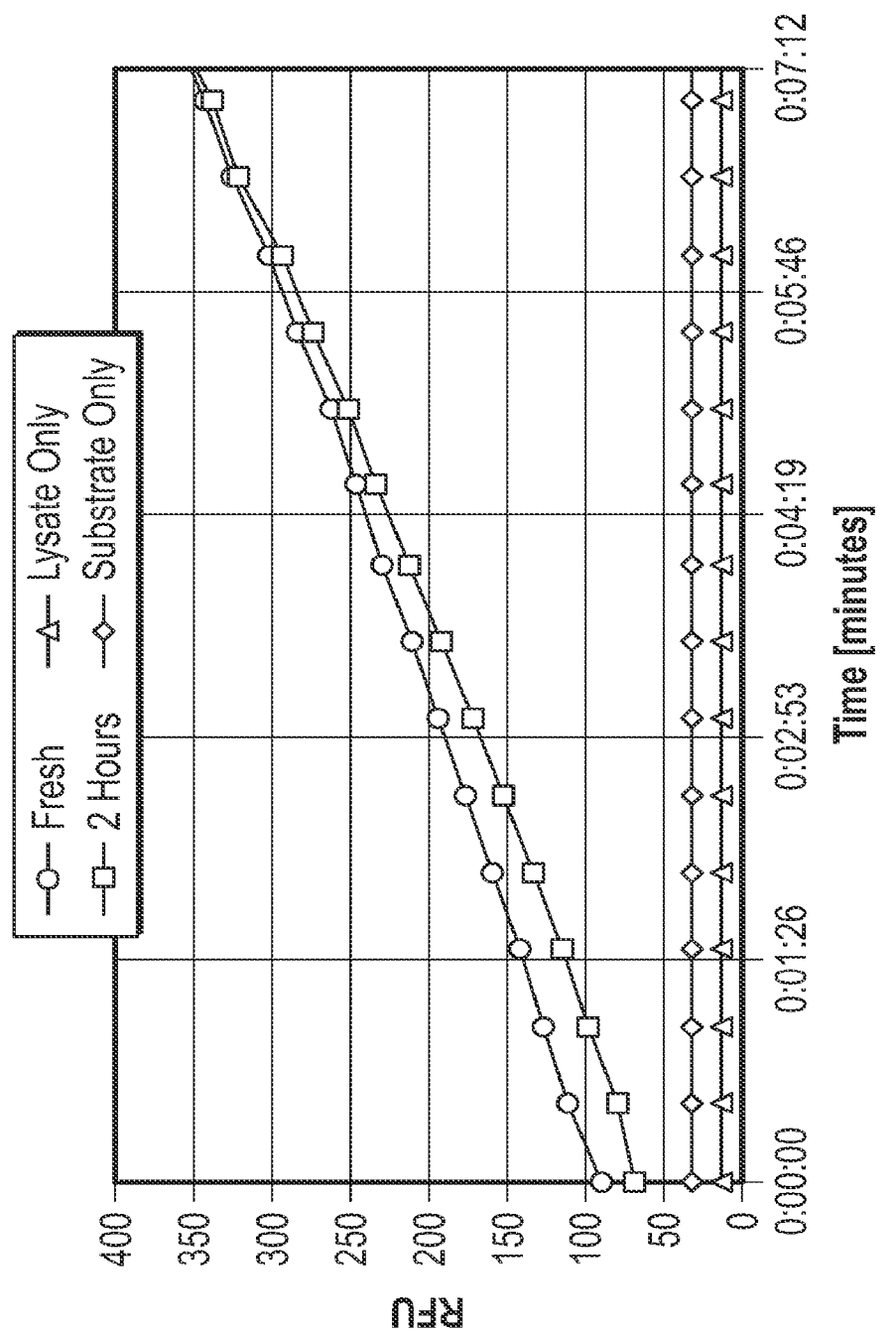
FIG. 6 is a graph showing fluorescence of the FRET substrate of FIG. 3 in fresh crude lysate or in crude lysate that was stored at 4° C. for 2 hours.
Figure 7:
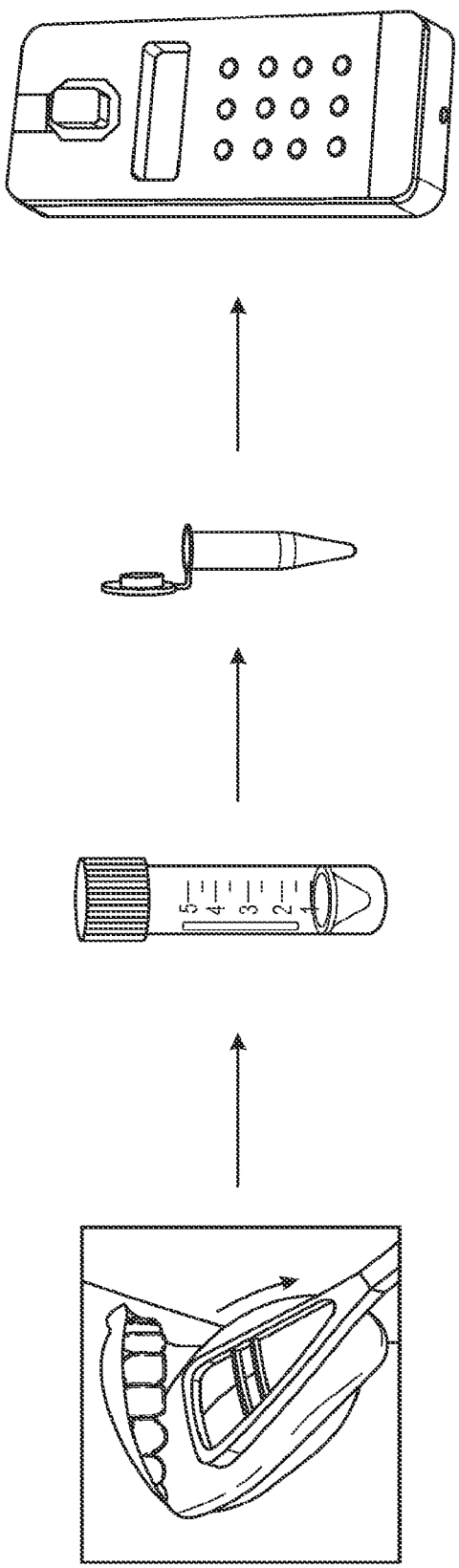
FIG. 7 is a diagram showing the test procedure to detect a pathogen.

FIG. 6 shows a progress curve using the FRET substrate of FIG. 3 in fresh crude lysate or in crude lysate that was stored at 4° C. for 2 hours. FIG. 7 shows a schematic of the enzymatic test procedure. A tongue scrape specimen is lysed in a vial containing lysis buffer, and the lysate transferred to a vial containing the reaction components in a freeze-dried form. The vial is inserted into the measurement port of a fluorometer and the fluorescence increase measured. FIG. 8 shows a calibrator curve of serial dilutions of unconjugated 7-amino-methylcoumarin (AMC).

Figure 11:
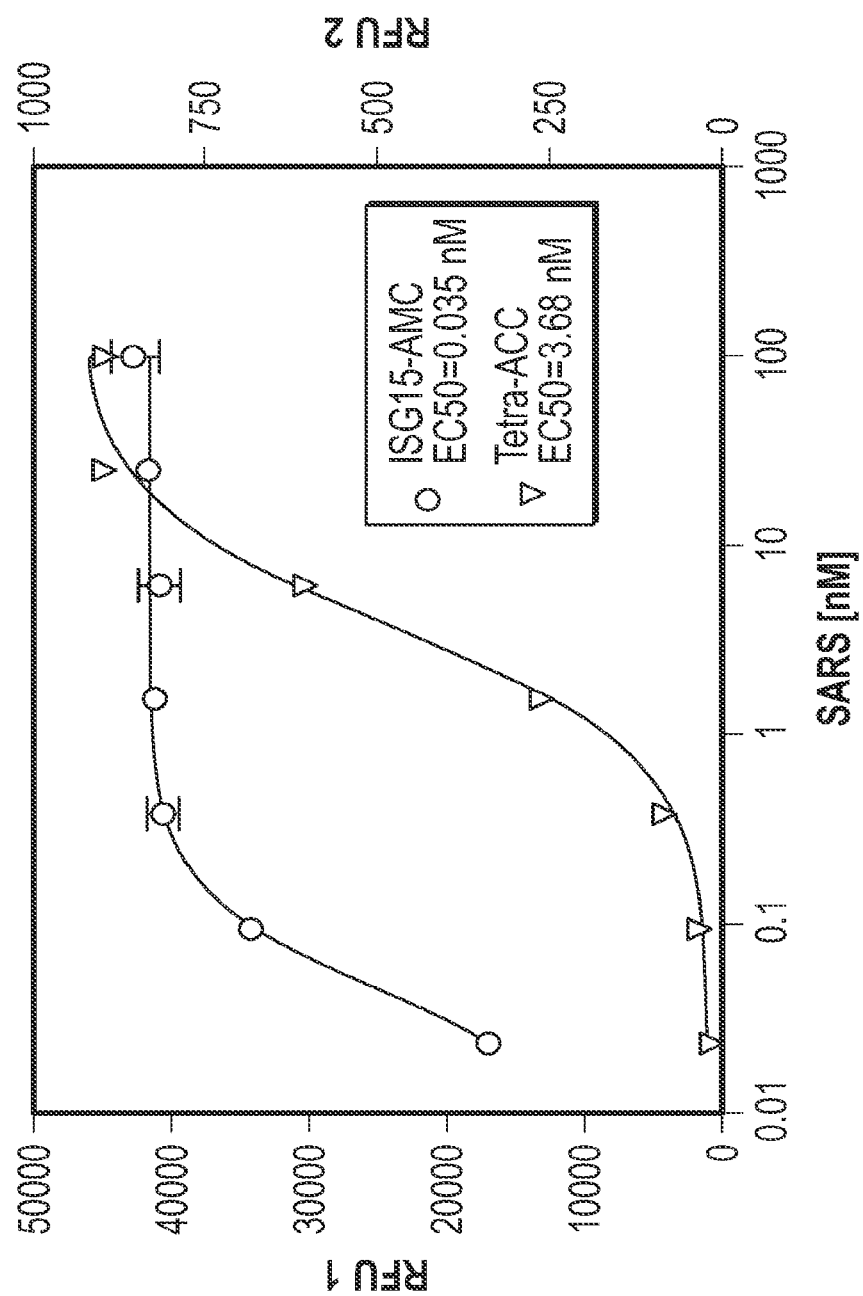
FIG. 11 is a graph showing an enzyme concentration curve using recombinant SARS PLpro and ISG15-AMC (circles) or L-R-G-G-AMC (SEQ ID NO. 5) (triangles)
Figure 12:
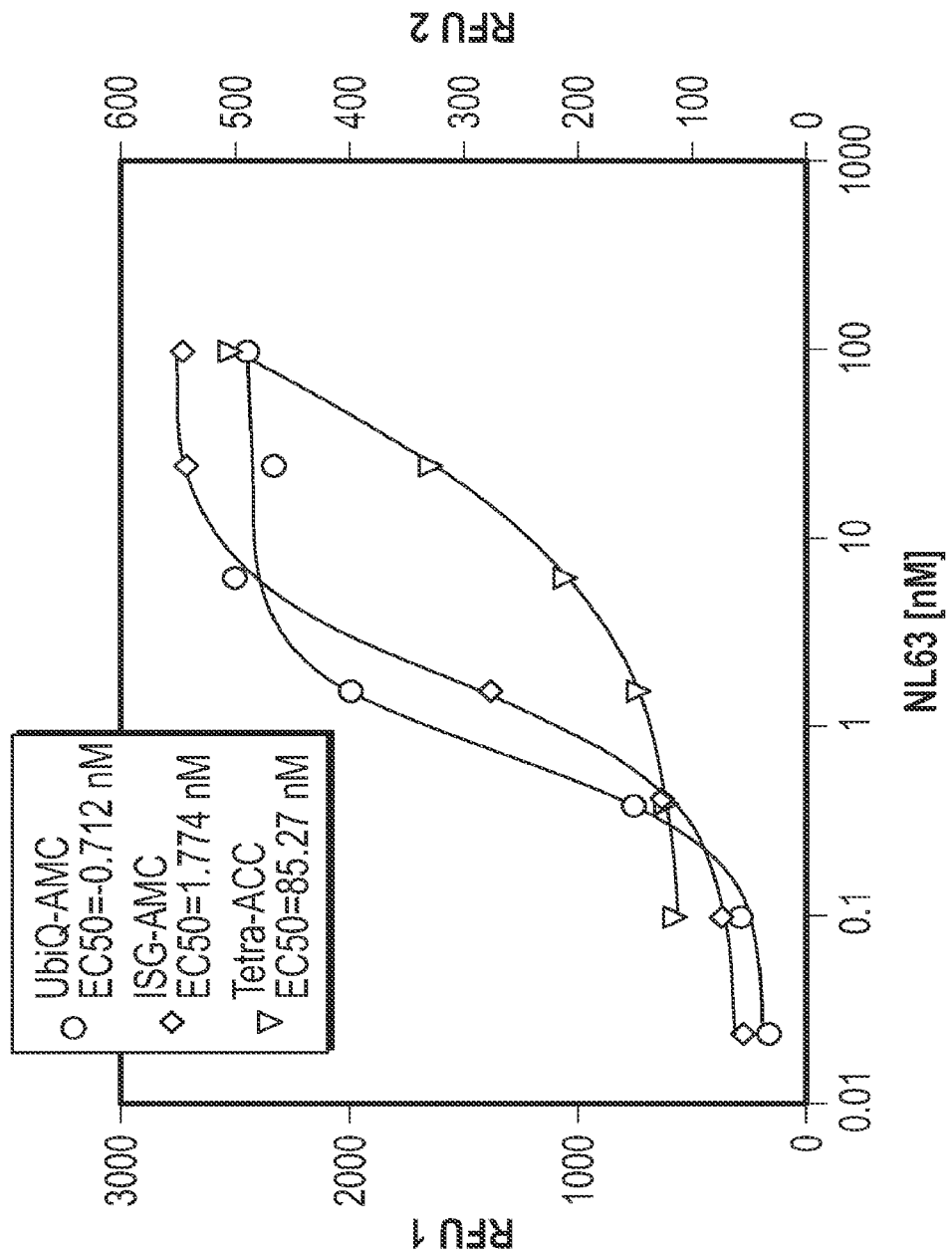
FIG. 12 is a graph showing an enzyme concentration curve using recombinant NL62 PLP2 and Ubiquitin-AMC (circles), ISG15-AMC (squares), or tetrapeptide-AMC (triangles)

FIG. 9 shows a schematic of a lateral flow assay based on the SARS protease cleavage assay. Substrates are labeled with histidine (His-6) and biotin (black circle) and reacted with PLpro enzyme. A mixture of cleavage products is generated containing uncleaved fragments or the peptidic fragment and biotin. The mixture is added to the sample pad of a lateral flow device and the fragments moved to the absorption pad by capillary flow. Uncleaved fragments and free biotin are captured by streptavidin on the strip. Cleaved fragments are captured by immobilized anti-histidine antibodies and detected by labeled anti-substrate antibodies. FIG. 10 shows a progress curve using either peptide with the amino acid sequence L-R-G-G-AMC (SEQ ID NO. 5) or Tyr-Dap-G-G-AMC in the presence (+) or absence (−) of crude tongue scrape lysate. The peptide with the sequence Tyr-Dap-G-G is not cleaved by endogenous enzymes present in lysate, whereas L-R-G-G (SEQ ID NO. 1) is cleaved. FIG. 11 shows an enzyme concentration curve using recombinant SARS PLpro and ISG15-AMC (circles) or L-R-G-G-AMC (SEQ ID NO. 5) (triangles). SARS PLpro cleaves the substrate ISG15, which contains the tetrapeptide cleavage sequence L-R-G-G (SEQ ID NO. 1) at its carboxyterminus, around 105 times more efficiently than the tetrapeptide L-R-G-G (SEQ ID NO. 1) alone. FIG. 12 shows an enzyme concentration curve using recombinant NL62 PLP2 and Ubiquitin-AMC (circles), ISG15-AMC (squares), or tetrapeptide-AMC (triangles). NL63 PLP2 cleaved ubiquitin 2.5 times more efficiently than ISG15 and 120 times more efficiently than the tetrapeptide.

Figure 13:
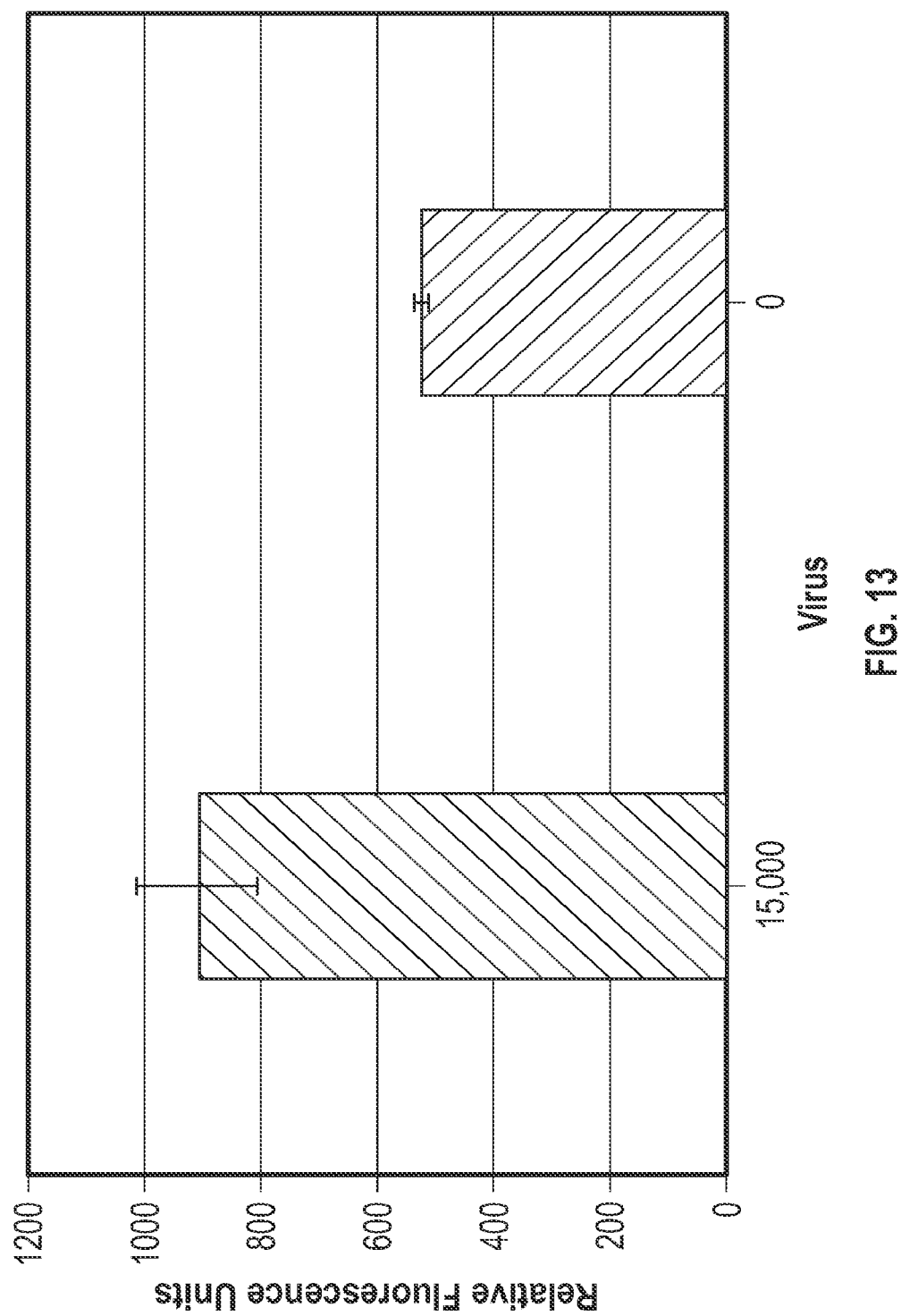
FIG. 13 is a graph comparing ISG15-AMC cleavage between crude lysates from infected human cells and uninfected lysates.
Figure 14:
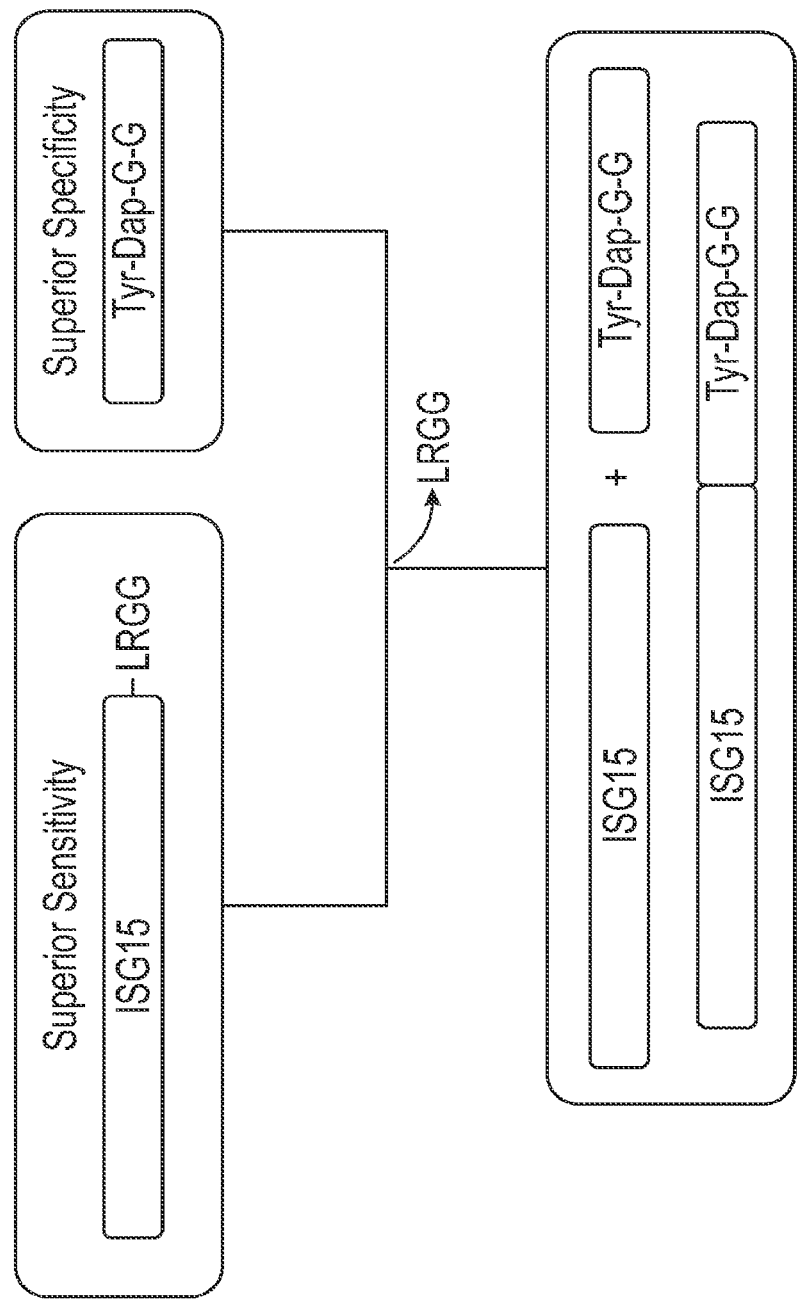
FIG. 14 is a schematic showing a peptide combination that results in superior sensitivity conferred by the ISG15 substrates and specificity conferred by the tetrapeptide sequence Tyr-Dap-G-G.

FIG. 13 shows an in vivo experiment that compares ISG15-AMC cleavage between crude lysates from 5970 human cells infected with 15,000 229E coronaviruses and uninfected lysates. FIG. 14 shows a schematic showing a peptide combination that results in superior sensitivity conferred by the ISG15 substrates and specificity conferred by the tetrapeptide sequence Tyr-Dap-G-G. The data in FIG. 13 show that coronavirus protease activity was detectable in as few as 6,000 cells that were infected with 15,000 229E coronaviruses. In clinical samples, it is expected to obtain around 800,000 shed epithelial cells/test (100 µl) in saliva or from tongue scrapes, of which 5-10% (40,000-80,000 cells) can be infected. This translated to an average of 10× more cells than are detectable in the in vivo model test with 6,000 cells. By comparison, current antigen tests required 2 million to 20 million viral copies for detection. The enzymatic test is thus more than 300 times more sensitive than antigen tests. RT-PCR tests require between 500-80,000 copies/ml while the enzymatic activity test is within an order of magnitude of this sensitivity, and given the advantages of this test, equals RT-PCR in clinical samples.

FIG. 15 shows an in vivo test using crude lysates from human cells that were infected with 229E, 0043 or NL63 coronaviruses. The cleavage of substrates Tyr-Dap-G-G, L-R-G-G (SEQ ID NO. 1), mono-ubiquitin (UbiQ) and ISG15 was shown as the percent fluorescence increase relative to uninfected cells. Cleavage was measured after 15 minutes (*), 60 minutes (), and 800 minutes (*). In vivo studies on human coronavirus strains 0043, 229E and NL63 with the enzymatic activity assay showed that the strains have different preferences for various substrates that contain the cleavage site L-R-G-G (SEQ ID NO. 1) at the C-terminus.

Figure 16:
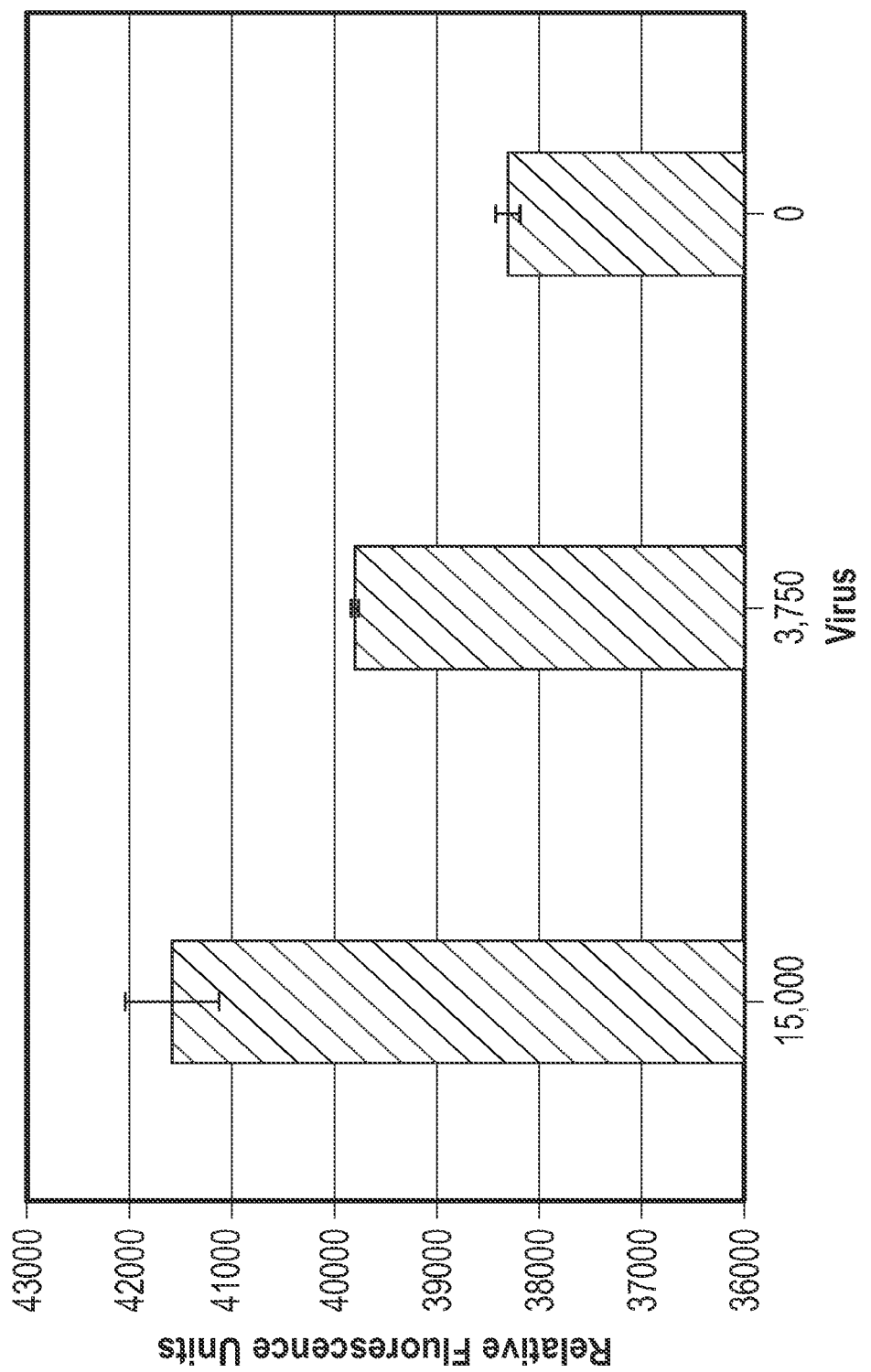
FIG. 16 is a graph showing cleavage of the ACE2-FITC substrate in crude lysates from infected human cells.

FIG. 16 shows an in vivo test in which crude lysates from human cells that were infected with 15,000, 3,750, or 0 229E coronaviruses cleave the ACE2-FITC substrate from FIG. 3.

Figure 17:
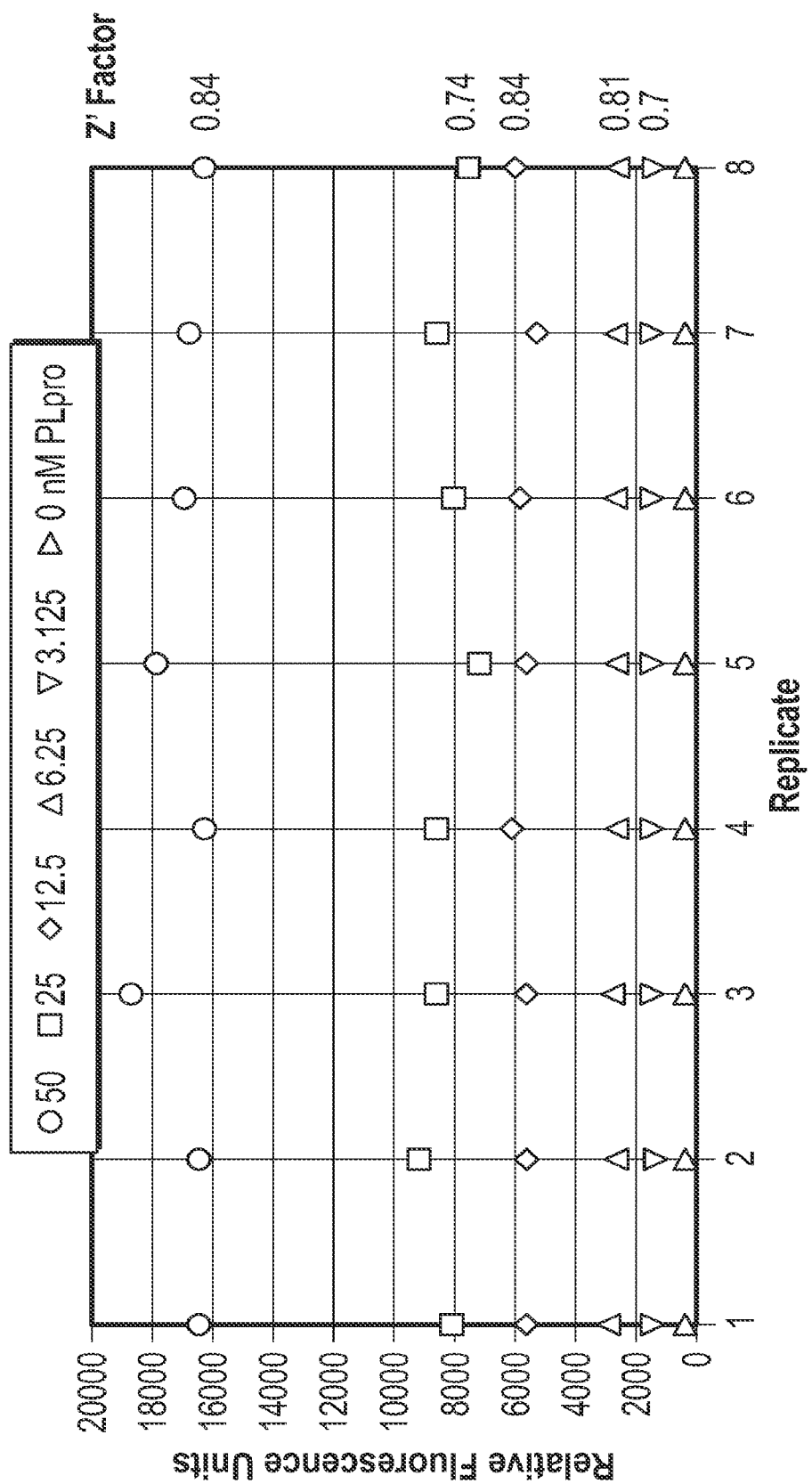
FIG. 17 is a graph showing florescence from the substrate L-R-G-G-AMC (SEQ ID NO. 5) and various concentrations of recombinant SARS PLpro enzyme.

FIG. 17 shows a test in which florescence from eight replicates of wells containing the substrate L-R-G-G-AMC (SEQ ID NO. 5) and various concentrations of recombinant SARS PLpro enzyme were measured to determine the Z'.

INDUSTRIAL APPLICABILITY

The invention is further illustrated by the following non-limiting examples. The ubiquitin used in experiments was a monoubiquitin. In addition, the tests used, for example, a panel of synthetic or recombinant ubiquitins that contain all eight native-linked diubiquitin conjugates: M1 (linear), K6, K11, K27, K29, K33, K48 and K63 linked. Other branched and linear ubiquitins are available. The preference for the substrates was determined in a competitive assay using the ubiquitins together with AMC or ACC-labeled tetrapeptide and recombinant PLpro or PLP enzyme from each coronavirus. The higher the fluorescence recorded, the lower the preference for binding and cleaving the unlabeled ubiquitin. Alternatively, direct labeled substrates may be used and cleavage measured in a direct, non-competitive assay. This approach delivers specific cleavage fingerprints of different human coronaviruses, e.g., from HCoV SARS-1, SARS-2, MERS, 229E, NL64, HKU1, 0043 that allow identifying the causative coronaviruses and distinguishing respiratory infections caused by coronavirus from other viruses that do not have deISGlating and deubiquitinylating activities, such as for example influenza, syncytial, parainfluenza viruses.

Example 1

Homogeneous SARS PLpro protease activity assay in crude lysate was assessed. PLpro activity may be detected using peptide substrates based on the amino acid sequence L-R-G-G (SEQ ID NO. 1) that is tagged with the fluorophore 7-amino-methylcoumarin (AMC). When cleavage occurred between the terminal glycine and AMC, fluorescence was released and was monitored using excitation and emission wavelengths of 365 nm and 465 nm, respectively.

Assays were performed in 7.5 μl volumes in 384-well plates at room temperature containing 50 μM substrate and recombinant SARS PLpro (100 nM; BPS Biosciences) in 50 mM HEPES, pH 7.0, 5 mM DTT. Cells were harvested from tongue scrapes and the cells lysed in $ddH_20$ containing various detergents. 7.5 μl of the crude lysate was added to the reaction mixture in the wells and the reaction progress was monitored at room temperature in 1-minute intervals using a plate-based fluorometer (Molecular Devices). The increase in fluorescence was measured as a function of enzyme activity. The control well did not contain recombinant enzyme. The slight fluorescence increases in the control well were due to cleavage of the substrate L-R-G-G-AMC (SEQ ID NO. 5) by endogenous enzymes present in the lysate. A substrate with artificial amino acids (Tyr-Dap-G-G) was not cleaved in crude human lysate.

Example 2

ACE2 was used as an internal control in crude lysate. An internal control, Angiotensin-Converting Enzyme2, was used to confirm that lysates were of sufficient quality and quantity for the assay to be performed. Fluorescence increase was monitored using a FRET peptide substrate with the sequence FITC-C6-Tyr-Val-Ala-Asp-Ala-Pro-Lys (Dnp)-OH (SEQ ID NO. 6). Fluorescein isocyanate (FITC) was quenched by dinitrophenyl (DNP). The substrate (5 μM) was diluted in 2× assay buffer (50 mM HEPES, pH 7.0, 5 mM DTT) and crude lysate was added to obtain a final volume of 15 μl in a well of a 384-well plate. The reaction progress was monitored in 1-minute intervals using a plate-based fluorometer with excitation and emission wavelengths of 490 nm and 515 nm. It was observed that fluorescence increased as a function of the number of coronaviruses used to infect cells, indicating increased ACE2 activity (or caspase activity) in cells with higher viral load.

Example 3

A multiplexed PLpro/ACE2 assay was performed. Reactions were performed as described in Example 1 and 2 in one vial and the fluorescence of each fluorophore was measured in a volume of 80 μl. The solution was prepared in a 0.5 ml real time PCR tube which was inserted into a battery-operated fluorometer. The fluorescence from the reactions was measured consecutively by switching from channel 1 (λexc=365 nm/λem=465 nm) to channel 2 (λexc=490 nm/λem=520 nm) by the push of a button.

Example 4

Lysate stability was measured. The activity of crude lysate from a tongue scrape sample stored for 2 hours on ice was compared to crude fresh lysate from the same individual. The fluorescence from the ACE2 reactions was measured in 1-minute intervals using λexc=490 nm and λem=520 nm in a plate-based fluorometer. Lysate without substrate and substrate without lysate were used as controls.

Example 5

Viral load was quantitatively measured. The fluorescence from unconjugated fluorophore, for example 7-amino-methycoumarin (AMC), was used to calculate the number of viruses that are present in a crude lysate that tested positive for PLpro activity. To this end, a calibrator curve was prepared containing several dilutions of AMC and the fluorescence was compared to the fluorescence obtained from a serial dilution of PLpro. To normalize for the amount of lysate present, a protein binding or DNA intercalating dye was used, such as Quantifluor or Hoechst 33258.

The preceding examples can be repeated with similar success by substituting the generically or specifically described components and/or operating conditions of embodiments of the present invention for those used in the preceding examples.

Note that in the specification and claims, "about" or "approximately" means within twenty percent (20%) of the amount or value given.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguring their relationships with one another.

SEQUENCE LISTING

```
Sequence total quantity: 6
SEQ ID NO: 1            moltype = AA  length = 4
FEATURE                 Location/Qualifiers
REGION                  1..4
                        note = synthetic construct
```

-continued

```
source              1..4
                    mol_type = protein
                    organism = synthetic construct
SEQUENCE: 1
LRGG                                                                    4

SEQ ID NO: 2        moltype = AA  length = 7
FEATURE             Location/Qualifiers
REGION              1..7
                    note = synthetic construct
source              1..7
                    mol_type = protein
                    organism = synthetic construct
SEQUENCE: 2
YVADAPK                                                                 7

SEQ ID NO: 3        moltype = AA  length = 6
FEATURE             Location/Qualifiers
REGION              1..6
                    note = synthetic construct
source              1..6
                    mol_type = protein
                    organism = synthetic construct
SEQUENCE: 3
YVADAP                                                                  6

SEQ ID NO: 4        moltype = AA  length = 5
FEATURE             Location/Qualifiers
REGION              1..5
                    note = synthetic construct
VARIANT             3
                    note = X can be any naturally occurring amino acid
source              1..5
                    mol_type = protein
                    organism = synthetic construct
SEQUENCE: 4
RLXGG                                                                   5

SEQ ID NO: 5        moltype = AA  length = 5
FEATURE             Location/Qualifiers
REGION              1..5
                    note = sythetic construct
VARIANT             5
                    note = X can be any naturally occurring amino acid
source              1..5
                    mol_type = protein
                    organism = synthetic construct
SEQUENCE: 5
LRGGX                                                                   5

SEQ ID NO: 6        moltype = AA  length = 7
FEATURE             Location/Qualifiers
REGION              1..7
                    note = synthetic construct
SITE                7
                    note = X - Lys(Dinitrophenol)
source              1..7
                    mol_type = protein
                    organism = synthetic construct
SEQUENCE: 6
YVADAPX                                                                 7
```

What is claimed is:

1. A method for detecting a coronavirus, the method comprising:
   providing a specimen, wherein the specimen comprises a plurality of cells;
   contacting the specimen with a first substrate, wherein the first substrate comprises a first signaling moiety conjugated to a carboxy terminus of the first substrate, the first substrate further comprising an Interferon Stimulated Gene-15 (ISG-15) or a fragment thereof, a ubiquitin or a fragment thereof, or a coronavirus protein fragment, and wherein the first substrate is cleaved by a coronavirus enzyme;
   contacting the specimen with a second substrate, wherein the second substrate comprises a control peptide and a second signaling moiety conjugated to the control peptide, wherein the second substrate is cleaved by an internal control enzyme;
   determining the presence of a first fluorescent signal from an unconjugated first signaling moiety produced by the coronavirus enzyme cleaving the first substrate wherein the presence of the first fluorescent signal indicates a presence of the coronavirus in the specimen;
   determining the presence of a second fluorescent signal from an unconjugated second signaling moiety produced by the internal control enzyme cleaving the control peptide wherein the presence of the second fluorescent signal indicates a presence of the internal control enzyme within the cell; and determining the first fluorescent signal from the unconjugated first signaling moiety and the second fluorescent signal from the unconjugated second signaling moiety to detect the coronavirus, the internal control enzyme or both in the specimen.

2. The method of claim 1, wherein the first substrate is added directly to live cells within the specimen.

3. The method of claim 1, further comprising lysing the plurality of cells prior to contacting the specimen with the first substrate.

4. The method of claim 1, wherein the coronavirus is severe acute respiratory syndrome coronavirus 2 (SARS-CoV-2).

5. The method of claim 1, wherein the internal control enzyme is angiotensin-converting-enzyme (ACE2).

6. The method of claim 1, wherein the coronavirus enzyme is papain-like protease (PLpro).

7. The method of claim 1, further comprising quantifying an amount of the coronavirus present in the specimen by comparing the first fluorescent signal to a calibration curve of relative fluorescence versus a fluorophore concentration.

8. The method of claim 1, wherein the first signaling moiety comprises rhodamine 110 and wherein the determining the presence of the first fluorescent signal comprises exciting the rhodamine 110 with a first wavelength of light and detecting the first fluorescent signal at a second wavelength of light different from the first wavelength of light.

9. The method of claim 1, wherein the first substrate comprises ISG-15 or an ISG-15 fragment and a ubiquitin or a ubiquitin fragment.

10. The method of claim 1, wherein the ISG-15 fragment comprises a sequence selected from (SEQ ID NO. 1), (SEQ ID NO. 4), (SEQ ID NO. 5), (SEQ ID NO. 6), (SEQ ID NO. 7), (SEQ ID NO. 8), (SEQ ID NO. 9), (SEQ ID NO. 10), (SEQ ID NO. 11), (SEQ ID NO. 12) and (SEQ ID NO. 13).

11. The method of claim 1, wherein the specimen is provided in a plurality of wells within a multi-well plate and the multi-well plate comprises a calibrator within at least one well.

12. The method of claim 1, wherein the specimen is provided in a plurality of wells within a multi-well plate and further comprising quantifying the coronavirus load within a well.

13. The method of claim 1, wherein the specimen is provided in a plurality of wells within a multi-well plate and the plate includes a positive control and a negative control.

14. The method of claim 1, wherein the specimen is provided in a plurality of wells within a multi-well plate and further comprising treating the specimen with an antibody and subsequently transfecting the plurality of cells with a substrate.

15. The method of claim 1, wherein the specimen is provided in a plurality of wells within a multi-well plate and further comprising treating the specimen with an antibody and subsequently transfecting the plurality of cells with the first substrate.

16. The method of claim 1, wherein the specimen is provided in a plurality of wells within a multi-well plate and further comprising treating the specimen with an antibody and subsequently transfecting the plurality of cells with the second substrate.

17. The method of claim 1, wherein the specimen is provided in a plurality of wells within a multi-well plate and further comprising treating the specimen with an inhibitor.

18. The method of claim 1 further comprising differentiating between a first coronavirus comprising a first coronavirus enzyme and a second coronavirus comprising a second coronavirus enzyme by comparing the first fluorescent signal from the unconjugated first signaling moiety cleaved from the first substrate by the first coronavirus enzyme over a period of time with the first fluorescent signal from the unconjugated first signaling moiety cleaved from the first substrate by the second coronavirus enzyme over the period of time.

19. The method of claim 1 further comprising deriving the first substrate from a selected one of at least two different species to identify the coronavirus.

20. The method of claim 1, wherein the first substrate further comprises a quencher comprising an organic dye or a molecule with an amide bond, and wherein the first signaling moiety is a fluorophore comprising xanthene dyes, coumarins, benzamide dyes, phenathridine dyes, acridine dyes, cyanine dyes, carbazole dyes, phenoxazine dyes, porphorin dyes, quinoline dyes, or a combination thereof.

21. The method of claim 1, wherein the first substrate further comprises a quencher comprising an organic dye or a molecule with an amide bond, and wherein the first signaling moiety is a fluorophore comprising aminomethyl coumarin (AMC), aminocarbomylcoumarin (ACC), rhodamine 110, or a combination thereof.

22. The method of claim 1, wherein the second substrate further comprises a quencher comprising an organic dye or a molecule with an amide bond, and wherein the second signaling moiety is a fluorophore comprising xanthene dyes, coumarins, benzamide dyes, phenathridine dyes, acridine dyes, cyanine dyes, carbazole dyes, phenoxazine dyes, porphorin dyes, quinoline dyes, or a combination thereof.

23. The method of claim 1, wherein the second substrate further comprises a quencher comprising an organic dye or a molecule with an amide bond, and wherein the second signaling moiety is a fluorophore comprising aminomethyl coumarin (AMC), aminocarbomylcoumarin (ACC), rhodamine 110, or a combination thereof.

* * * * *